US008725311B1

(12) United States Patent
Breed

(10) Patent No.: US 8,725,311 B1
(45) Date of Patent: May 13, 2014

(54) DRIVER HEALTH AND FATIGUE MONITORING SYSTEM AND METHOD

(75) Inventor: David S Breed, Miami Beach, FL (US)

(73) Assignee: American Vehicular Sciences, LLC, Plano, TX (US)

( * ) Notice: Subject to any disclaimer, the term of this patent is extended or adjusted under 35 U.S.C. 154(b) by 78 days.

(21) Appl. No.: 13/419,988

(22) Filed: Mar. 14, 2012

Related U.S. Application Data

(60) Provisional application No. 61/452,469, filed on Mar. 14, 2011, provisional application No. 61/547,798, filed on Oct. 17, 2011.

(51) Int. Cl.
*G05D 1/00* (2006.01)

(52) U.S. Cl.
USPC .................. 701/1; 600/300; 600/529

(58) Field of Classification Search
USPC ............. 701/1, 42, 45; 600/300, 529; 348/77, 348/E07.085; 345/440
See application file for complete search history.

(56) References Cited

U.S. PATENT DOCUMENTS

| | | |
|---|---|---|
| 3,947,815 A | 3/1976 | Muncheryan |
| 4,706,072 A | 11/1987 | Ikeyama |
| 4,836,219 A | 6/1989 | Hobson et al. |
| 5,573,012 A | 11/1996 | McEwan |
| 5,583,590 A | 12/1996 | Clupper |
| 5,691,693 A | 11/1997 | Kithil |
| 5,766,208 A | 6/1998 | McEwan |
| 5,844,486 A | 12/1998 | Kithil et al. |
| 5,846,206 A | 12/1998 | Bader |
| 5,907,282 A | 5/1999 | Tuorto et al. |
| 6,011,477 A | 1/2000 | Teodorescu et al. |
| 6,014,602 A | 1/2000 | Kithil et al. |
| 6,060,989 A | 5/2000 | Gehlot |
| 6,091,334 A | 7/2000 | Galiana et al. |
| 6,104,296 A | 8/2000 | Yasushi et al. |
| 6,147,612 A | 11/2000 | Ruan et al. |
| 6,208,264 B1 | 3/2001 | Bradney et al. |
| 6,275,146 B1 | 8/2001 | Kithil et al. |
| 6,445,988 B1 | 9/2002 | Breed et al. |
| 6,616,613 B1 | 9/2003 | Goodman |
| 6,669,632 B2 | 12/2003 | Nanba et al. |
| 6,684,973 B2 | 2/2004 | Baba et al. |
| 6,757,602 B2 | 6/2004 | Breed et al. |
| 6,816,077 B1 | 11/2004 | Shieh et al. |
| 6,822,573 B2 * | 11/2004 | Basir et al. .................... 340/575 |
| 6,960,841 B2 | 11/2005 | Saitou et al. |

(Continued)

FOREIGN PATENT DOCUMENTS

WO 2011046178 A1 4/2011

*Primary Examiner* — Thomas Black
*Assistant Examiner* — Luke Huynh
(74) *Attorney, Agent, or Firm* — Brian Roffe

(57) ABSTRACT

Vehicle including a seat in which an occupant sits during use of the vehicle and a monitoring system for monitoring the occupant in the seat. The monitoring system includes sets of electric field antennas, each including at least one antenna, a control unit connected to the antenna sets and including selectors coupled to the antennas. The selectors are controlled by the control unit to obtain signals from one or more antennas serving as receiving antennas and one or more antennas serving as sending antennas. The control unit determines which combination of sending antenna(s) and receiving antenna(s) provides a strongest signal in an expected heartbeat range and/or expected respiration range of the occupant and then monitors this combination for changes and/or deviations from a normal range of heartbeats and/or respiration.

25 Claims, 10 Drawing Sheets

(56) References Cited

U.S. PATENT DOCUMENTS

| | | |
|---|---|---|
| 6,993,378 B2 | 1/2006 | Wiederhold et al. |
| 7,196,629 B2 | 3/2007 | Ruoss et al. |
| 7,215,991 B2 | 5/2007 | Besson et al. |
| 7,277,741 B2 | 10/2007 | Debreczeny et al. |
| 7,397,382 B2 | 7/2008 | Ikegami et al. |
| 7,652,583 B2 | 1/2010 | Sanchez et al. |
| 7,666,151 B2 | 2/2010 | Sullivan et al. |
| 7,822,453 B2 | 10/2010 | Mannheimer et al. |
| 8,068,942 B2 | 11/2011 | Breed |
| 8,098,165 B2 | 1/2012 | Demirdjian et al. |
| 8,152,198 B2 | 4/2012 | Breed et al. |
| 8,562,526 B2 | 10/2013 | Heneghan et al. |
| 2002/0140215 A1 | 10/2002 | Breed et al. |
| 2003/0136600 A1 | 7/2003 | Breed et al. |
| 2006/0167595 A1 | 7/2006 | Breed et al. |
| 2006/0251293 A1 | 11/2006 | Piirainen et al. |
| 2007/0025597 A1 | 2/2007 | Breed et al. |
| 2007/0086624 A1 | 4/2007 | Breed et al. |
| 2007/0116327 A1 | 5/2007 | Breed et al. |
| 2008/0015801 A1 | 1/2008 | Sharma |
| 2008/0045847 A1 | 2/2008 | Farag et al. |
| 2010/0087748 A1 | 4/2010 | Tobola et al. |
| 2010/0234747 A1 | 9/2010 | Hatakeyama |
| 2011/0224875 A1* | 9/2011 | Cuddihy et al. ............... 701/42 |
| 2012/0259181 A1* | 10/2012 | Fujita et al. ............... 600/300 |

* cited by examiner

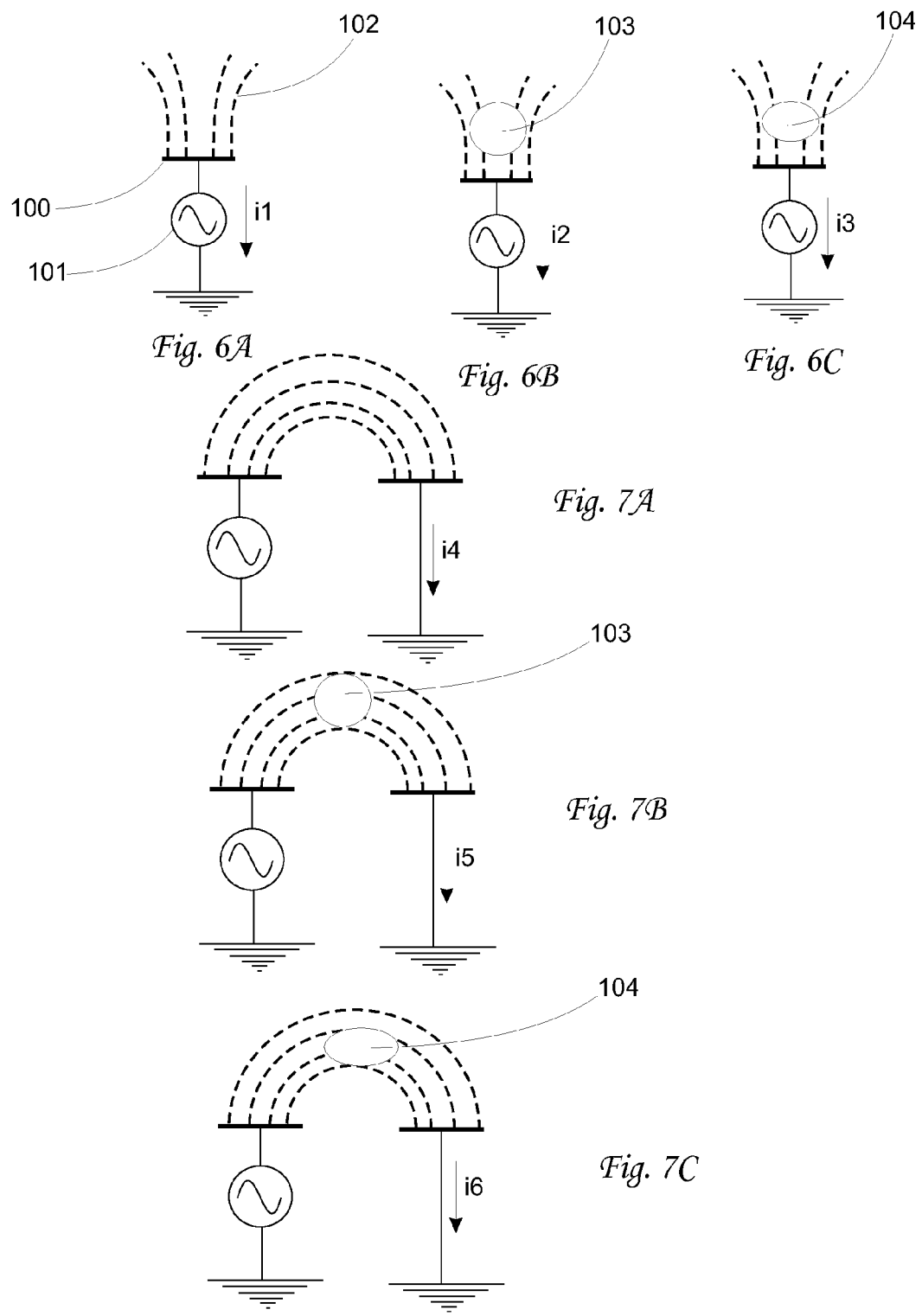

DRIVER HEALTH AND FATIGUE MONITORING SYSTEM AND METHOD

CROSS REFERENCE TO RELATED APPLICATIONS

This application claims priority under 35 U.S.C. §119(e) of U.S. provisional patent application Ser. Nos. 61/452,469 filed Mar. 14, 2011 and 61/547,798 filed Oct. 17, 2011, both of which are incorporated by reference herein.

FIELD OF THE INVENTION

The present invention relates generally to systems and methods for monitoring a driver of a vehicle to determine at least one characteristic, condition, property and/or state of the driver, for example, whether the driver is falling asleep or otherwise unable to operate the vehicle.

BACKGROUND OF THE INVENTION

There are several different vehicular situations that are lumped together and called the distracted or inattentive driver problem. These situations include cases where the driver is wide-awake but eating, putting on make-up, texting and talking on the phone; cases where the driver is physically fatigued and may or may not also be sleepy; medical condition cases where the driver suffers a medical condition such as a stroke or heart attack; cases where the driver is under the influence of alcohol or drugs; and cases where the driver is just sleepy. At least one embodiment of the present invention is primarily concerned with detecting a drowsy or sleepy driver but a number of the other causes of the distracted driver also affect the parameters that are the focus of embodiments of the invention and thus will also be addressed, and are encompassed within the scope of the invention in its entirety. A primary focus of at least one embodiment of the present invention is to measure the heartbeat rate and respiration rate of the driver using electric fields or optics, and through analysis of these rates, predict whether the driver is losing his/her ability to safely operate the vehicle. Driver inattention is a larger problem than driving sleepiness and fatigue.

One study found that fatigue plays a significant role in around 20% of all fatal crashes. Another reported that about 58% of one hundred-seven single-vehicle roadway departure crashes were fatigue-related.

Fatigue has been defined as "a state of reduced physical or mental alertness which impairs performance" (Williamson, A., Feyer, A. and Friswell, R. (1996). The impact of work practices on fatigue in long distance truck drivers. *Accident Analysis and Prevention*, 28(6), 709-719). Dingus, T., McGehee, D., Hulse, M., Jahns, S., Manakkal, N., Mollenhauer, M., and Fleischman, R. (June, 1995). TravTek evaluation task C3 camera car study. Pub. No. FHWA-RD-94-076. Washington, D.C.: U.S. Department of Transportation, Federal Highway Administration.) states that fatigue is "a neurobiological process directly related to the circadian pacemaker in the brain and to the biological sleep need of the individual" and cannot be "prevented by any known characteristics of personality, intelligence, education, training, skill, compensation, motivation, physical size, strength, attractiveness or professionalism". Note that fatigue and drowsiness are not the same thing. Some of the indicators of drowsiness include a person having their eyes closed for long time, sudden head movements, touching the face with a hand, strong blinking and yawning. In the medical area, drivers suffering from obstructive sleep apnea syndrome (OSAS) have an increased risk for being involved in motor-vehicle collisions. One of every five adults has at least mild Obstructive Sleep Apnea (OSA), and one of fifteen has at least moderate OSA. OSA has many negative effects, including excessive daytime sleepiness, increased risk of motor vehicle accidents, hypertension, psychological distress, and cognitive impairment. Apnea is generally considered the cessation of airflow for ten seconds or longer, and obstructive sleep apnea is apnea that occurs in spite of respiratory effort.

Alcohol and drugs can contribute to drowsiness. In one study in Italy, a significant number of drivers killed in single vehicle automobile accidents had consumed drugs. Cocaine was found to be the most frequently detected substance (9.5%), then benzodiazepines (7.5%), methadone, morphine and marijuana (THC) (3.5%). In 5.5% of subjects, more than one substance was found.

Use of drugs was found in another study to affect respiration rates. In all of the drugs tested as surrogates for morphine and heroine, inspiration was always depressed and there was a selective depression of expiration.

A large number of patents and technical papers address systems for detection of a drowsy driver but despite the potential for such systems, researchers have been largely unsuccessful in finding a feasible way to identify sleepiness or inattention. Nevertheless, it has been demonstrated that this can be done using an EEG. As one study reported "By combining power spectrum estimation, principal component analysis and artificial neural networks, we show that continuous, accurate, noninvasive, and near real-time estimation of an operator's global level of alertness is feasible using EEG measures." (Estimating Alertness from the EEG Power Spectrum, January, 1997). However, attaching electrodes to a driver is intrusive and is not a practical solution to drowsiness detection. The disclosure below uses at least one electrical, physical, chemical and/or biological property of a driver, such as can be obtained by EEG- and EKG-signals, respiration, oxygen saturation, temperature, perspiration, etc., to reliably determine drowsiness in time to prevent accidents, see, for example, U.S. Pat. No. 7,215,991. This is accomplished unobtrusively without physically interacting and contacting with the driver, i.e., without attaching electrodes to the driver.

Another recently introduced product makes use of a cap which places electrodes on the skull or the operator and measures an approximate EEG and from the measurements attempts to determine whether the operator is fatigued. See WWW.smartcap.com.au.

Optical Applications

Many systems have been described in the patent and non-patent literature that attempt to use optical methods, such as video cameras, to detect blinking, head movement, yawning etc., as indications of the drowsy driver. The most successful study has led to the development of the PERCLOS method whereby the percentage of time that the eyes are closed is used to measure drowsiness. Unfortunately, none of these systems have demonstrated a forecasting success rate that permits action to be taken in time for the driver to get to a location where he/she can exit the road in time. Studies have shown that only ECG measurements have this ability to predict that a driver is falling asleep. At least one embodiment of the present invention, when using optical techniques for example, provides a method of measuring the heartbeat and respiration rates optically that, with appropriate analysis of the variability of these rates, will achieve a highly accurate prediction of the drowsiness state of the driver.

Previous studies have shown that eye closure occurrences dramatically increase during a 10-second period preceding an accident and propose that the monitoring such closures could allow the car to take some form of automated response to wake up the driver, e.g., a loud noise, a bright light, possibly even the activation of an "autopilot" if that capability is developed. Unfortunately, a 10-second warning is insufficient for the driver to find an exit and pull off of the road even if he/she accepts the warning of the vehicle system. Such systems must also be careful of a false alarm and thus must err on the side of not taking a drastic action.

It is also known that the duration of the eye closures one minute before an accident is much higher than at earlier times and partial eye closures (measured by the ratio between horizontal and vertical portions of the visible pupil) have been shown to be a way to detect drowsiness as much as about 10-12 minutes prior to an accident. However, measuring eye closures is hampered by a driver wearing glasses, hats or other apparatus which shades the eyes from the camera, intensity of ambient light (e.g., sunlight) and in variation in the eye shape from person to person. Temporary medical conditions, including use of medications, also can affect both the blink rate and the percentage of the eye that is closed. Thus, although there have been numerous studies and many systems developed, none has been deployed due to these and other factors. As one study reported, "The original aim of this project was to use the retinal reflection (only) as a means to finding the eyes on the face, and then using the absence of this reflection as a way of detecting when the eyes are closed. It was then found that this method might not be the best method of monitoring the eyes for two reasons. First, in lower lighting conditions, the amount of retinal reflection decreases; and second, if the person has small eyes, the reflection may not show." Or as reported in another study, "Overall, the measures of driver drowsiness based on physical changes in the eye are developing into a technology that could potentially be used on the road. These approaches have a fundamental problem, however, in that the changes being measured are likely to be occurring late in the process of fatigue. It is possible that the driver has been through a significant period of high crash risk due to lowered alertness before significant eye closure effects are able to be detected. As a tool for fatigue prevention therefore, they will be signaling late stage fatigue and sleepiness when there are relatively few options for recovery apart from a period of sleep. Other problems associated with the eye- and face-change detection technologies, are deciding on the point at which the driver is in an unsafe state and when a warning should be applied, and deciding on the nature of the warning signal itself." (Williamson, A., Chamberlain, T. "Review of on-road driver fatigue monitoring devices", NSW Injury Risk Management Research Centre, University of New South Wales, April, 2005).

A commonly available device, the pulse oximeter, uses light to determine the pulse rate of a patient as well as the amount of oxygen in the blood. This is a device that usually clips to a finger, ear lobe or other part of the body, i.e., physically interacts and contacts the patient's body. It will be disclosed below that this can also be accomplished in an unobtrusive manner for the driver of a vehicle. As reported in U.S. Pat. No. 7,277,741, pulse oximetry takes advantage of the fact that in live human tissue, hemoglobin is a strong absorber of light between the wavelengths of 500 and 1100 nm. Pulsation of arterial blood through tissue is readily measurable, using light absorption by hemoglobin in this wavelength range. A graph of the arterial pulsation waveform as a function of time is referred to as an optical plethysmograph. The amplitude of the plethysmographic waveform varies as a function of the wavelength of the light used to measure it, as determined by the absorption properties of the blood pulsing through the arteries. By combining plethysmographic measurements at a plurality of different wavelength regions where oxy- and deoxy-hemoglobin have different absorption coefficients, e.g., two such wavelengths, the oxygen saturation of arterial blood can be estimated. Typical wavelengths employed in commercial pulse oximeters are 660 nm and 890 nm.

U.S. Pat. No. 7,822,453 further shows that an oximetry sensor can work on the forehead, although this is done by placing the sensor on the forehead. In addition, U.S. Pat. Appln. Publ. No. 20080045847 discloses that a non-contact, passive method for measurement of arterial pulse from areas such as the major superficial arteries of the body through analysis of thermal IR images acquired by passive thermal IR imaging sensors. The output waveform readily contains the information on heart rate, cardiac interbeat intervals, heart-rate variability and other features inherent in arterial pulse.

Other methods in the prior art are set forth in the following patent publications. U.S. Pat. No. 7,666,151 discloses use of piezoelectric film placed on a seat or bed surface that obtains a measure of both heartbeat and respiration rates. In this application, this concept is extended in what is considered an unobvious manner to use of a fluid-filled bladder weight sensor and load cell weight sensors as further methods of obtaining the heartbeat and respiration rates. Recently, The Plessey corporation has announced an EPIC ECG sensor (PS2501) which can be held in the hands of a patent and obtains the ECG signal. There is indication that this or a similar sensor can also do so if it is placed in the seatback in close proximity to the back of the driver. By whatever method is used, the analysis of these signals to obtain a measure of drowsiness is not believed to have previously been applied.

U.S. Pat. No. 6,822,573 discloses use of a geophone in the seat and also steering wheel-based sensors for heartbeat measurement, but does not disclose how to analyze this information to obtain a measure of drowsiness.

Assignee's U.S. Pat. Nos. 6,078,854, 6,253,134, 6,397,136, 6,330,501, 6,445,988, 6,474,683, 6,735,506, 6,736,231, 6,757,602, 6,950,022, 6,793,242, 7,050,897, 7,786,864 and 7,889,096 disclose general and radar methods for determining heartbeat rate as have others, such as a more recent U.S. Pat. No. 7,196,629 assigned to Bosch. Improvements to radar-based systems are also disclosed herein.

Analysis

Analysis of human heartbeat and respiration rates and in particular their variability during waking and sleeping has been reported in the literature. For example, a simple observation that the heartbeat rate shows less variability when sleeping but shows a noticeable jump on waking can be detected and used for drowsiness detection. As shown by several simulator tests, a driver often experiences a succession of micro-sleeps for several minutes prior to an accident. Thus, on a preliminary basis, the variability of the basic heartbeat rate shows a period of low variability followed by a jump on waking for each of these micro-sleeps and can, when applied in one embodiment of the invention, be a reliable predictive measure of drowsiness leading to an accident with a several minute lead time.

Spectral analysis of heart rate variability is well established as reported in (T. Penzel, J. W. Kantelhardt, H. F. Becker, J. H. Peter, A. Bunde, "Detrended Fluctuation Analysis and Spectral Analysis of Heart Rate Variability for Sleep", Hospital of Philipps-University, Marburg, Germany, Nov. 16, 2003): "The physiological interpretation of the very low-frequency (VLF) component (<0.04 Hz) is still discussed, the low-frequency (LF) component (0.04-0.15 Hz) reflects baroreflex sympathetic control of blood pressure, and the high-frequency (HF) component (0.15-0.4 Hz) reflects respiratory rhythm and is believed to be related to parasympathetic control of heart rate."

From Wikipedia: "Sympathetic and parasympathetic divisions typically function in opposition to each other. This natural opposition is better understood as complementary in nature rather than antagonistic. For an analogy, one may think of the sympathetic division as the accelerator and the parasympathetic division as the brake. The sympathetic division typically functions in actions requiring quick responses. The parasympathetic division functions with actions that do not require immediate reaction. A useful acronym to summarize the functions of the parasympathetic nervous system is SLUDD (salivation, lacrimation, urination, digestion and defecation)."

A discussion of respiration variability can be found in U.S. Pat. No. 7,397,382. ". . . a depth of breathing of a person is detected, and drowsiness of the person is determined when the depth of breathing falls in a predetermined breathing condition including at least one of a sudden decrease in the depth of breathing and a periodic repetition of deep breathing and shallow breathing." " . . . the thorax pressure generally changes in a fixed manner when a person condition changes from awakened to drowsing. When the person starts to feel drowsy from the awakened condition or from the rest condition, the depth and period of breathing does not remain stable and the breathing sometimes cannot be found. In this instance, the depth of the breathing suddenly becomes shallow or alternately becomes deep and shallow in three to seven breaths. When the person falls asleep, the breathing is repeated periodically although the depth of breathing slightly changes." This patent uses a steering wheel-mounted sensor to detect the driver's pulse and then derives a measure of respiration from the pulse signal. This is dependent on the driver gripping the steering wheel where the sensor is located with sufficient force as to allow accurate measurements to be made. This condition is generally not reliably achieved in practice due to the many forms of driver steering wheel interaction, especially when drowsiness in occurring. Such a system, for example, will not work if the driver is wearing thick gloves.

Countermeasures

Various studies have evaluated the effects of various countermeasures. One study evaluated a fatigue warning system that used ocular and face monitoring, vehicle speed, steering position and lane position. They found that in spite of frequent warnings, users of the system did not take more or longer breaks. Drivers generally ignored the warning signals received. The physical aspect of the warning signals used in the study had no impact on driver fatigue levels. Voluntary rest stops, lasting on average about thirty minutes, only had a minor impact on decreasing driver fatigue with short-lived effects. The authors concluded that voluntary breaks were ineffective in substantially counteracting the effects of fatigue associated with prolonged night-time driving.

In contrast, Mercedes Benz has developed a technology reminder on the series E-Class cars in the year 2010. This technology is able to monitor seventy different parameters to detect fatigue without reporting on what these parameters were. If drowsiness is detected, a coffee cup icon and the words "time to rest" appears on the dashboard panel accompanied by the sound of car alarms to remind the driver so as not to fall asleep while driving. Reduction of accidents due to this system is recorded to be one-third of the total rate.

Another reported technique for detecting drowsiness is by monitoring a response of the driver. This involves periodically requesting the driver to send a response to the system to indicate alertness. A problem with this technique is that it will eventually become tiresome and annoying to the driver. This reported technique thus teaches away from this concept which is used in some embodiments of the invention. This very useful technique must be applied in such a manner that it does not become tiresome to the driver.

Until now, use of heartbeat and respiration variability monitoring through electric field, optical, Plessey ECG sensors or weight monitoring systems to detect drowsiness in vehicle occupants has not previously been disclosed, to the extent this field has been investigated by the inventor. Additional background of the invention is found in the related applications. All of the patents, patent applications, technical papers and other references mentioned herein are incorporated by reference in their entirety.

Technical papers and other published documents that are particularly relevant to the inventions described herein include:

1. Borgobello, Bridget "MIT developing webcam-based health monitoring minor". Press release MIT News Office, Oct. 5, 2010.
2. J. Smith, T. White, C. Dodge, J. Paradiso, N. Gershenfeld, D. Allport "Electric Field Sensing for Graphical Interfaces". 1998, IEEE Comput. Graph. Appl.
3. "Location Privacy And Wireless Body Area Networks", The Physics asXiv Blog, MIT Technology Review, Mar. 23, 2011.
4. Richards, Austin, *Alien Vision: Exploring the Electromagnetic Spectrum with Imaging Technology* (SPIE Press Monograph Vol. PM104), 2001, ISBN 0-8194-4142-2
5. Poh, et al. "Non-contact, automated cardiac pulse measurements using video imaging and blind source separation", Optics Express, Vol. 18, Issue 10, pp. 10762-10774 (2010).
6. W. J. Cui, L. E. Ostrander, and B. Y. Lee, "In vivo reflectance of blood and tissue as a function of light wavelength," IEEE Trans. Biomed. Eng. 37(6), 632-639 (1990).
7. Grubb et at, "Towards Forehead Reflectance Photoplethysmography to Aid Delivery Room Resuscitation in Newborns", 4th European Conference of the International Federation for or Medical and Biological Engineering 23-27 Nov. 2008, Antwerp, Belgium (IFMBE Proceedings).
8. *"Location Privacy And Wireless Body Area Networks" The Physics arXiv Blog, MIT Technology Review,* 03/23/11.
9. W. W. Wierwille "Overview of Research on Driver Drowsiness Definition and Driver Drowsiness Detection", Paper No. 94 S3 0 07, Virginia Polytechnic Institute and State University May 23, 1994.
10. J. A. Paradiso, N. Gershenfeld, "Musical Applications of Electric Field Sensing", Computer Music Journal 1997.
11. Tzyy-Ping Jung, Scott Makeig, Magnus Stensmo, Terrence J. Sejnowski, "Estimating Alertness from the EEG Power Spectrum", IEEE Transactions On Biomedical Engineering, VOL. 4, NO. I, J MAR) 1997.
12. D. W. Rowe, J. Sibert, D. Irwin, "Heart Rate Variability Indicator of User State as an Aid to Human-Computer Interaction", CHI '98 Proceedings of the SIGCHI conference on Human factors in computing systems, 1998.
13. James Nolan, MD; Phillip D. Batin, MD; Richard Andrews, MRCP; Steven J. Lindsay, MRCP; Paul Brooksby, MD; Michael Mullen, MRCP; Wazir Baig, MD; Andrew D. Flapan, MD; Alan Cowley, FRCP; Robin J. Prescott, PhD; James M. M. Neilson, PhD; Keith A. A. Fox, FRCP, "Prospective Study of Heart Rate Variability and Mortality in Chronic Heart Failure", Circulation. 1998; 98:1510-1516, doi: 10.1161/01.CIR.98.15.1510, (Circulation. 1998; 98:1510-1516.), 1998 American Heart Association, Inc.

14. "Drowsiness Detector (Stanford MS EE Project)—MIT Media Lab.", May 30, 2001.
15. "Eye-Activity Measures of Fatigue and Napping as a Fatigue Countermeasure", Final Report, USDOT, FHWA-MC-99-028, January, 1999.
16. N. Parmar "Drowsy Driver Detection System", Design project, Department of Electrical and Computer Engineering, Ryerson University. 2002.
17. Smith, P.; Shah, M.; da Vitoria Lobo, N., "Monitoring Head Eye Motion for Driver Alertness with One Camera", Pattern Recognition, 2000. Proceedings. 15th International Conference on, Issue Date: 2000, On page(s): 636-642, vol. 4.
18. K. Willson, D. P. Francis, R. Wensel, A. J. S. Coats, and K. H. Parker, "Detrended Fluctuation Analysis and Spectral Analysis of Heart Rate Variability for Sleep", 2002 Physiol. Meas. 23 385 doi:10.1088/0967-3334/23/2/314.
19. S. Yu. Chekmenev, H. Rara, and Aly A. Farag, "Non-contact, Wavelet-based Measurement of Vital Signs using Thermal Imaging", ICGST Int J Graph Vision Image Process 2006; 6:25-30. 35.
20. Amy Diane Droitcour, "Non-contact measurement of heart and respiration Rates with a single-chip microwave doppler radar", Stanford University Doctoral Dissertation, June, 2006.
21. W. Jiang, Z. Chongxunr, L. Guohua and D. Ming, "A New Method for Identifying the Life Parameters via Radar", URASIP Journal on Applied Signal Processing, Volume 2007 Issue 1, 1 Jan. 2007.
22. E. P. Scilingo, A. Lanat, D. Zito, D. Pepe, "Wearable monitoring of cardiopulmonary activity through radiant sensing". Proceedings of the phealth2008.
23. J. F. Layerle, X. Savatier, J. Y. Ertaud, "Catadioptric Sensor for a Simultaneous Tracking of the Driver's Face and the Road Scene" The 8th Workshop on Omnidirectional Vision, Camera Networks and Non-classical Cameras—OMNIVIS, Marseille: France (2008).
24. G. D. Furman, A. Baharav, C. Cahan, "Early Detection of Falling Asleep at the wheel" Cardiology, 2008, 2008—ieeexplore.ieee.org.
25. Bridget Borgobello, "MIT developing webcam-based health monitoring minor", MIT News Office, Oct. 5, 2010.
26. Furman, G. D.; Baharav, A, "Investigation of Drowsiness while Driving Utilizing Analysis of Heart Rate Fluctuations", IEEE Conference on Computing in Cardiology, 2010, Issue Date: 26-29 Sep. 2010, page(s): 1091-1094.27. Kate Greene, "Talking to the Wall", MIT Technology Review May 3, 2011.

U.S. patents that are particularly relative to the inventions described herein include the following in addition to those referenced in the text:
27. U.S. Pat. No. 6,684,973, entitled "Occupant detecting apparatus"
28. U.S. Pat. No. 6,816,077, entitled "Multiple sensor vehicle occupant detection"
29. U.S. Pat. No. 6,960,841, entitled "Passenger detection system and detection method"

Possible definitions of terms used in the application are set forth in U.S. patent application Ser. No. 10/940,881, incorporated by reference herein.

SUMMARY OF THE INVENTION

A vehicle including a seat in which an occupant, such as a driver, sits during use of the vehicle, and a monitoring system for monitoring the occupant in said seat. The monitoring system includes a plurality of sets of electric field antennas, each set including at least one antenna and more likely a plurality of antennas, and a control unit connected to the antenna sets and that includes selectors coupled to said antennas and that controls the selectors to obtain signals from one or more of said antennas serving as receiving antennas and one or more of said antennas serving as sending antennas. After obtaining signals from multiple combinations of the antennas, and maybe even all of the possible combinations of antennas, the control unit determines which combination of one or more of said antennas serving as the sending antennas and one or more of said antennas serving as the receiving antennas provides a strongest signal in an expected heartbeat range and/or expected respiration range of the occupant. Thereafter, the control unit monitors this determined combination for changes and/or deviations from a normal range of heartbeats and/or respiration rate, and preferably only this determined combination. Changes and/or deviations from the normal range of heartbeats and respiration rate may be used to assess the drowsiness or sleepiness of the occupant, especially when the driver of the vehicle, and activate a notification system that requires a response to enable continued operation of the vehicle by the driver.

A method for monitoring an occupant of a vehicle, especially the driver of a vehicle, includes arranging a plurality of antennas on a seat, each separated from one another; selecting from a plurality of different possible combinations of the antennas, two or more of the antennas to form a sending and receiving arrangement of antennas, generating a weak electric field via the selected antenna arrangement, detecting information related to a current flow in the selected antenna arrangement during generation of the weak electric field, and determining, using a processor, a health condition of the occupant based on the detected information. The health condition includes, but is not limited to, the drowsiness or sleepiness of the driver.

BRIEF DESCRIPTION OF THE DRAWINGS

The following drawings are illustrative of embodiments of the system developed or adapted using the teachings of at least one of the inventions disclosed herein and are not meant to limit the scope of the invention as encompassed by the claims.

FIGS. 6A, 6B and 6C illustrate the principles of operation of a single electric field monitoring element in the presence of a body element and a modified body element.

FIGS. 7A, 7B and 7C illustrate the principles of operation of a pair of interacting electric field monitoring elements in the presence of a body element and a modified body element.

DETAILED DESCRIPTION OF THE INVENTION

Figure 1:
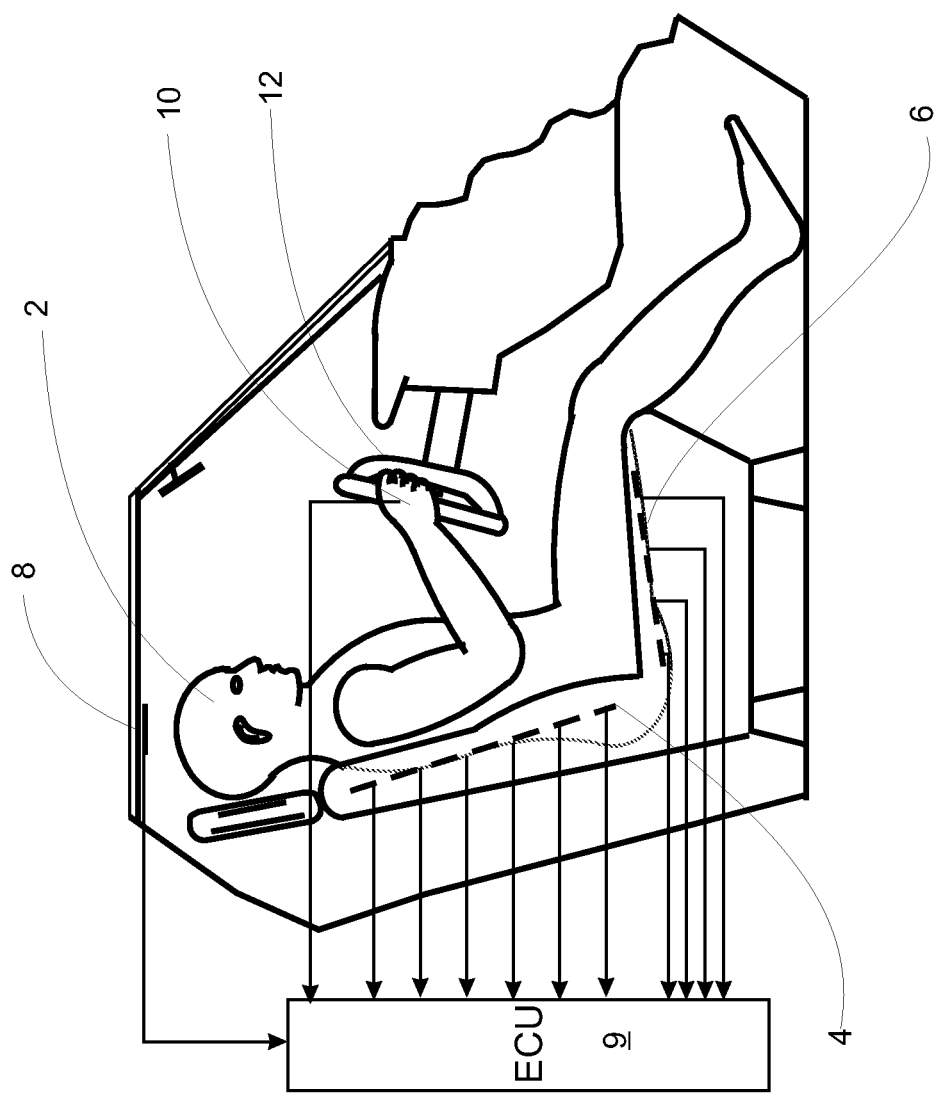
FIG. 1 is a side view with parts cutaway and removed of a vehicle showing the passenger compartment containing a driver sitting in a vehicle seat which contains a plurality of electric field antennas in accordance with a first embodiment of the invention.

All patents or literature referred to anywhere in this specification are incorporated by reference in their entirety. Also, although many of the examples below relate to a particular vehicle, an automobile, the invention is not limited to any particular vehicle and is thus applicable to all relevant vehicles including all compartments of a vehicle including, for example, the passenger or other compartment of an automobile, truck, farm tractor, construction machine, train, airplane and boat.

"Or" and "and" as used in the specification and claims shall be read in the conjunctive and in the disjunctive wherever they appear as necessary to make the text inclusive rather than exclusive, and neither of these words shall be interpreted to limit the scope of the text.

There is a continuing need to recognize when a driver or machine operator is distracted in order to regain his attention before an accident results from such distraction. Distraction can take many forms as described in the background section and each has a particular suit of solutions. A texting driver, for example, can be detected with a camera and appropriate pattern recognition software and/or by the electromagnetic emissions from his or her cellphone or other connected device being used to text. Similarly, a driver that is talking on a hand-held cellphone can be detected optically and/or by the electromagnetic emissions of his/her cell phone arising from the area of the driver seat. A particular sensor can be placed so as to monitor the driver seat or a pair of sensors that can determine the angle of arrival of the EM signal can be mounted on the dashboard, for example.

An inebriated driver can be detected, for example, by an alcohol monitor that samples air in the passenger compartment or by driver behavior monitoring or by monitoring his heartbeat and/or breathing (i.e., respiration rate). Driver behavior indicative of inebriation can be detected optically with pattern recognition software and/or by monitoring the driving behavior of the driver with respect to a map database and accurate vehicle location system or optically using a camera that monitors the vehicle position on the roadway. In both cases, pattern recognition software applied or executed by a computer or other processing unit can be trained to recognize abnormal behavior. Such pattern recognition software is typically embodied on non-transitory computer-readable media available to a processor that is coupled to any system that provides information about the driver or operator. The pattern recognition software may also be in the form of a computer program stored on non-transitory media and that may be installed on the vehicle prior to sale to the consumer. The software and computer program may be updated via a wired link or a wireless link, e.g., via the Internet or another communications network.

Detecting the drowsy or health impaired driver is a different issue generally requiring different hardware and software. Monitoring the eyes of the driver is one approach when the eyes are visible. However, it may be difficult to diagnose a driver having a heart attack by his eye motion, or lack thereof, in time to take remedial action. Also, a driver with sunglasses or even ordinary glasses or a hat with a shade or veil may present difficulties for eye tracking software and then the driver may not be looking at the camera at the time that an event occurs. A system that can work with eye trackers or independently is thus needed to sense cases missed by eye trackers or to confirm the eye tracker results in order to minimize false alarms.

Various solutions to detecting a drowsy driver or one that is having a heart attack, stroke or other health related event are disclosed in U.S. patents and published applications assigned to the assignee of this invention or its affiliated company, all of which are incorporated herein by reference, including: U.S. Pat. Nos. 5,829,782, 5,845,000, 20070025597, U.S. Pat. Nos. 6,116,639, 7,887,089, 7,769,513, 6,513,833, 7,660,437, 7,009,502, 6,950,022, 7,788,008, 7,676,062, 7,738,678, 6,793,242, 7,596,242, assigned at issuance to Automotive Technologies International, Inc. and 20080195261, U.S. Pat. Nos. 7,629,899, 7,983,802, and 7,295,925 assigned at issuance to Intelligent Technologies International, Inc. In these patents and published applications, the methods disclosed are optical, radar and driving behavior related, for example, to maps. Three methods that have not been discussed and will be discussed here are measuring: (1) the variations in pressure in a bladder or PDVF sheet caused by heartbeats and/or respiration rate, (2) the variations in the appearance of a patch of skin on the face of a driver due to heartbeat, respiration rate, blood pressure and temperature, and (3) the variations in capacitance or electric field signals also due to heartbeat and/or respiration rate. A fourth method has recently become available using Plessey PS2501 ECG sensors mounted in the seatback.

For these four methods, an electric field monitoring system is particularly useful especially since it is now in production as an occupant presence and position sensor. By monitoring driver heartbeat rates and/or respiration rates, a determination can be made as to whether the driver is drowsy and at risk of falling asleep and/or whether he or she is experiencing a health event that could interfere with his or her ability to operate a vehicle. The respiration rate is indicative of the driver's breathing and other parameters indicative of breathing may alternatively be used, i.e., not necessarily a rate at which the driver breathes or respires.

The facial monitoring approach, which is being developed at the MIT Media Lab and which has been considered for patient monitoring, uses a facial image to determine the flow of blood in the face vessels and then can derive an accurate pulse reading. The respiration rate and blood pressure readings can also be determined from the facial image. While these techniques are in the experimental stage, their incorporation into a vehicle for the purpose of driver health monitoring has not been considered by others and is believed to be unique to inventions disclosed herein. With this system, there is no need for other apparatus, only a camera that can view the driver's face with green and, in some cases, IR illumination. Neither green nor IR illumination has been disclosed in the MIT study, although green frequencies reflected from the face from natural or broad spectrum illumination is discussed. Thus, a single camera can determine eye tracking, closure state, blinking rate and pulse and respiration measurements, as well as blood pressure.

Apparatus have also been developed in Japan to remotely measure heart rate and respiration rate using low power microwaves. This is similar to use of radar as disclosed in patents mentioned herein and in U.S. Pat. No. 7,196,629. Also, as disclosed above, a smart cap can be used to measure certain EEG signals and can be used to determine operator fatigue.

The driver emits electromagnetic signals that are used in some Electroencephalogram (EEG) and electrocardiogram (EKG or ECG) devices to monitor brainwaves and electro cardio functions of the body and use of sensors placed in the seat, seatbelt, seatback and headrest to monitor these signals is also contemplated herein and some are discussed below. Other observables include IR radiation from the driver and particularly his or her face indicative of the driver's face or other location temperature. All of these monitoring techniques are included herein as driver health and condition monitoring systems.

All driver monitoring systems are imprecise and thus subject to false alarms and consequently, before any action is taken to take control of any vehicle systems, the diagnosis should ideally be verified through driver feedback. This feedback can take many forms such as employing a heads-up display on the windshield or elsewhere in the view of the driver that display a query asking the driver to respond, such as orally or by depressing the horn or other switch or button, or making a gesture, for example. Other feedback systems include an oral alarm or verbal statement requesting a response from the driver or any other visual or audible alarm or message requiring the driver's attention and subsequent action indicating that the sensed event was a false alarm. Failing to receive a proper response, the driver monitoring system can repeat the request a number of times, wherein the specific number may be dependent on or determined by the urgency of the situation (i.e., a more urgent situation might require more requests than a less urgent situation). In one example, the driver monitoring system can ask the driver "are you alright?" and if the driver responds with something like "yes", then the system can be reset. If the driver fails to respond to a simple verbal request for a simple verbal response, the request can be changed to a more complex request such as "if you are alright, depress the horn button or raise your hand." If the driver fails to respond appropriately to this more complex request, one or more of a variety of actions can be taken by the vehicle system depending on an assessment on the vehicle as to what is most appropriate.

Thus, the driver monitoring system in accordance with the invention includes an algorithm embodied on storage media that is accessed by the processor to select requests, i.e., a request selection algorithm, based in part on a history of requests that may be maintained in a memory unit also accessed by the processor. The actions that may be taken can include a gradual slowing of the vehicle and flashing the emergency lights, sounding the horn for example in a pulsed alarm mode, taking control of the steering to maintain the vehicle in its lane using lane monitoring cameras, if available, or GPS with an accurate map database if available, and avoiding a collision, notifying a remote site, allowing a remote site to assess the situation and take partial control of the vehicle, etc. The action or actions are determined by an action selection algorithm embodied on storage media that is accessed by the processor that can factor in various factors, including, for example, the severity of the situation.

A preferred system will first be disclosed based on an electric field occupant monitoring sensor system whereby the variations in the electric field strength at particular frequency ranges corresponding the human heartbeats (about 30 Hz to about 200 Hz) and respiration rates (about 0.05 to about 2 Hz). Since it is unlikely that steady signals from other sources will interfere with these frequency ranges, filtering and locking onto these signals and tracking them while searching for anomalies, using electronic hardware and software that is known to those skilled in the art, requires only straightforward signal processing that could be easily developed by one skilled in the art without undue or unreasonable experimentation. Gross occupant movement or even the movement of his or her extremities can also be monitored and, even without knowing the exact motion detected, this information can be used to collaborate the analysis of the respiration and heartbeat signals. Additionally, if the driver is also monitored by a camera, the accuracy and reliability of the entire system can be dramatically improved. The passenger can tell if the driver is having a heart attack or falling asleep. Therefore, an optical or other monitoring system can also do so. Adding in a heartbeat and/or respiration monitor should make the accuracy of such a system close to 100%.

1. Electric Field Driver Health Monitoring

Referring now to the accompanying drawings, FIG. 1 is a side view, with parts cutaway and removed of a vehicle showing the passenger compartment, or passenger container, containing a driver 2 operating a vehicle. Embedded in the seat or as part of the seat cover material are two sets of electric field antennas 4 and 6. The manner in which each set of electric field antennas 4, 6 can be embedded in the seat may be by placing the electric field antennas in the cushion material of the seat. To make the electric field antennas of the sets thereof 4, 6, part of the seat cover material, electrically conductive material may be woven into the material of the seat cover or arranged on the material of the seat cover. Other alternatives include placing a conductive mat in the seat just below the seat cover material or, in some cases using the seat heating wires as an antenna. There are thus many ways that an area of a seat can be made conductive and to function as an antenna.

Each set of electric field antennas 4, 6 can have any appropriate number of individual antennas such as from 2 to about 20. Antenna set 4 is illustrated with 7 antennas and antenna set 6 with 5 antennas. Antennas can additionally be placed at other convenient locations within the vehicle such as antenna 8 located on the ceiling or headliner above the seat or seating location in which the driver is expected to be present, and antenna 10 located on the steering wheel 12, and others not shown in FIG. 1 can be on the vehicle door and floor etc. Antenna 8 may be arranged on the exposed surface of the material forming the ceiling or headliner, or behind this surface. Antenna 10 may be arranged within the housing defining the steering wheel or on the outer surface thereof.

Each of the antennas is connected to an electronic control unit (ECU) 9 which performs the health monitoring calculations as explained below. ECU 9 includes software and hardware known to those skilled in the art, such as a processor and signal processing circuitry and software embodied on non-transitory computer-readable media to implement the processing stages described herein. The connections between the antennas and the ECU 9 may be a wired or wireless connection. As used herein, a "control unit" will generally mean any component or combination of components that is capable of processing input data and/or signals for an identified purpose, and generating from the data and/or signal processing, commands or signals to be directed to over one or more other electronic components to be controlled. A control unit in accordance with the invention may have other functions, e.g., to generate signals to be transmitted via a communications system.

Figure 2:
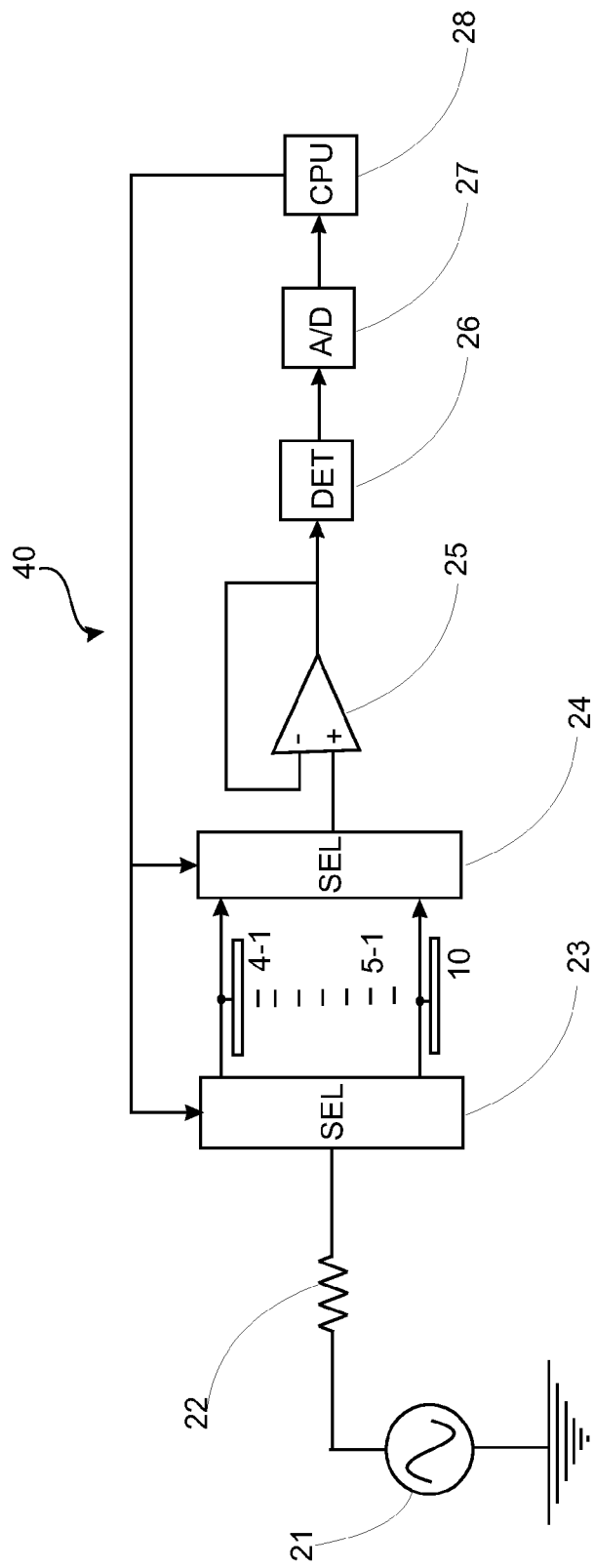
FIG. 2 is a block circuit diagram of the electric field sensing system of FIG. 1.

A representative circuit block diagram of the ECU 9 is illustrated generally at 40 in FIG. 2 for the sets of antennas illustrated in FIG. 1. One skilled in the art would understand how to implement this circuit block diagram in a commercial electronic package.

In the circuit block diagram 40, an oscillator 21 operating in a frequency range of, for example, about 100 kHz to about 10 MHz is attached to a resistor 22, a pair of selection switches 23 and 24, a voltage buffer 25, a detector 26, an A/D converter 27 and a processor 28. The antennas in the seatback or seat back portion (antenna set 4) are labeled 4-1 through 4-7 and the antennas in the seat bottom or seat bottom portion (antenna set 6) are labeled 5-1 through 5-5. The seat bottom portion is that portion of the seat on which the driver 2 sits while the seat back portion is that portion of the seat against which the driver's back rests. Not all antennas are individually labeled in FIG. 2, e.g., antenna 8. The function of the selection switches 23, 24 or selectors is to choose that combination of sending and receiving antennas that provide the best heartbeat, respiration and occupant movement signals. Instead of selection switches 23, 24, any type of selection device or selection means that performs the same function as selection switches 23, 24 may be used in the invention. Any of the antennas can operate in a sending mode or receiving mode and a single antenna can be both considered as a sender and receiver, that is, the occupancy of a seat can affect the antenna current.

An excellent background for the functioning of electric field occupant sensors is provided in U.S. Pat. Nos. 6,684,973 and 6,960,841 as well as others assigned to Elesys and Honda covering electric field occupant sensing and others assigned to Automotive Technologies International, Inc, (ATI) mentioned herein. Whereas Elesys and ATI primarily use this technology for identifying the occupancy of the passenger seat for the purposes of airbag suppression or depowered deployment, the purpose here is to use the technology in an altogether different manner to achieve health and fatigue monitoring of the driver.

To satisfy this object, among others, the variation in the electric field signal caused by the beating heart and respiration needs to be separated from the overall signal. Also, the antennas that provide the most information for occupant identification are not necessarily the same antennas that provide the best heartbeat or respiration signals. Further, the antennas that provide the best signal for heartbeat monitoring are not necessarily the same antennas that provide the best signal for respiration monitoring, however, the respiration rate can generally be derived from the heartbeat signal. Additionally, it is desirable to monitor various motions of the occupant as that can augment conclusions from the heartbeat and respiration monitors. Antennas that are best for motion monitoring are not necessarily the same ones that are best for identification or for heartbeat or respiration monitoring.

In current airbag systems, the driver often does not need to be classified for the purpose of airbag suppression so there is no need to install an electric field occupant monitor in the driver seat. It is typically assumed that the driver has the characteristics of an adult and that the airbag does not need to be suppressed unless the driver's seat is positioned far forward indicating that the driver is a small adult (a position-based determination of airbag suppression or control). This can be determined by a seat track sensor. Thus, previously, electric field sensors have not been installed in the driver seat for driver monitoring. Of course, if they have been installed for health monitoring, they can also be used for driver out-of-position sensing at little, if any, additional cost.

Selection switches 23, 24 in FIG. 2 can, in general, cycle through the various combinations of antennas while the processor 28 searches for the strongest signals in the expected heartbeat range and in the expected respiration range and once the strongest signal in each range is found, the processor 28 locks onto that signal and monitors it for changes and/or abnormalities. Such abnormalities can include slow or fast heartbeats or breathing, skipped beats, tachycardia, other irregular heart beats, irregular breathing, etc. As the driver moves, the best choice of antennas may change so the processor 28, while monitoring the chosen signals (selected at a preceding time), can continue to search for better signals (at the current time). In some cases, a single antenna may provide the best signal for the property to be monitored while, in others, a pair of antennas will yield a superior signal. Generally, the searching may be confined to single antennas or pairs of antennas but, in some cases, the best signal may come from one transmitting antenna and two or more receiving antennas.

Generally, for heartbeat and respiration monitoring, the best signals may come from antennas in the seatback whereas motion sensing antennas can involve any of the antennas. When a driver is leaning close to the steering wheel, the steering wheel-mounted antenna can provide a superior signal. The ceiling-mounted antenna also can provide occupant motion signals. Although not shown, a door mounted antenna can also provide valuable information.

Figure 3:
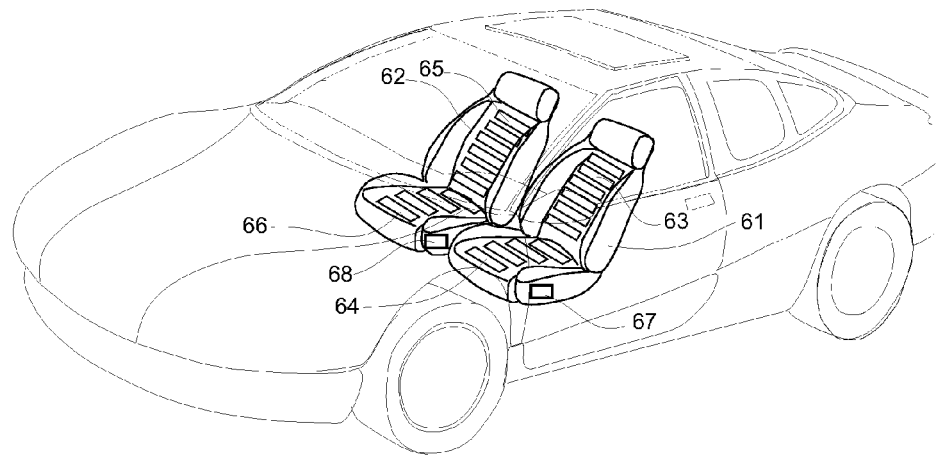
FIG. 3 is a perspective view with parts cutaway and removed of a vehicle showing the passenger compartment containing an electric field occupant sensing systems on both the driver and passenger seats in accordance with a second embodiment of the invention.

A perspective view with parts cutaway and removed of a vehicle showing the passenger compartment containing electric field occupant sensing systems associated with both the driver and passenger seats is illustrated in FIG. 3. Although the systems are shown to be the same on the driver and passenger seats, in fact, their function and mode of operation is different and this may dictate a different antenna arrangement for the various seats. Antenna sets or groups 65 and 66 associated with the passenger seat 62 are occupant classification sensors for the purpose of determining, for example, whether there is a child or a rear-facing child seat present or if the seat is unoccupied, in which case, the airbag will be suppressed or perhaps depowered. Antenna groups 65, 66 may be integrated into the passenger seat 62 in the same manner as antennas of the antenna sets 4, 6 are integrated into the seat.

The electric field system associated with the driver seat 61 appears to be the same, but the function is to monitor the heartbeat and respiration rate to determine whether the driver is falling asleep, having a heart attack or is otherwise unable to operate the vehicle. Processor 28, of the circuit black diagrams of the ECUs 67, 68 that may be the same as circuit block diagram 40 shown in FIG. 2, executes different routines for the different uses of the antenna systems.

In FIG. 3, the passenger seat 62 has electric field antenna sets or groups 65 and 66 and the driver seat 61 has electric field antenna sets or groups 63 and 64. Antenna groups 63, 64 may be integrated into the driver seat 61 in the same manner as antennas of the antenna sets 4, 6 are integrated into the seat. Each seat 61, 62 can have its own ECU labeled 67 in the driver seat 61 and 68 in the passenger seat 62. A single ECU could service both seats 61, 62 and the ECU(s) need not be located in the seats. ECU's 67, 68 may be arranged on the respective seat, in the respective seat or even separated from the seat, in all cases, coupled through wires or wireless to the respective antenna groups.

The heartbeat sensor, respiration sensor and motion sensors can be used with other occupant sensor systems. In this case, for example, the health and fatigue monitoring system can be only used on the driver seat and weight sensors based on strain gages or bladders, optical sensors, ultrasonic sensors, seat track and seatback sensors etc. can be used for passenger classification or, in the case of the seat track sensor, for driver classification.

Figure 4:
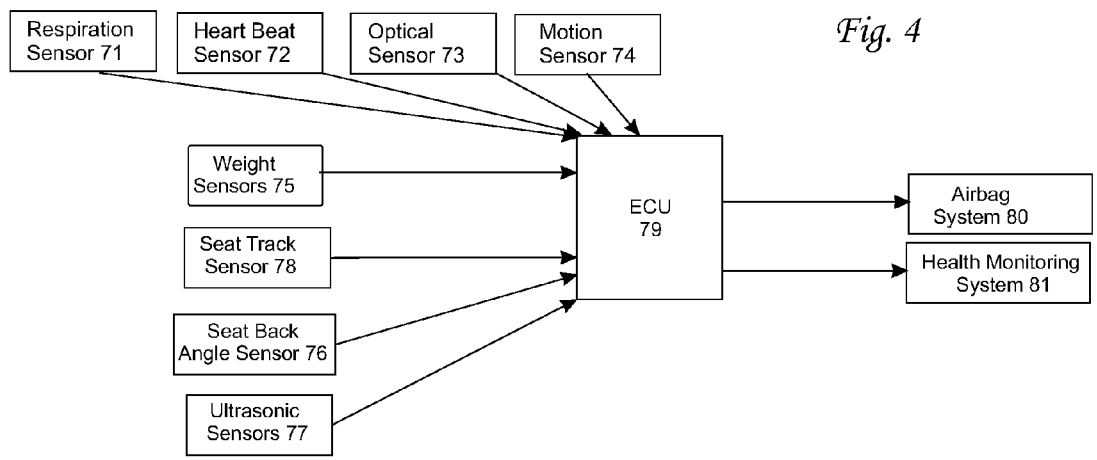
FIG. 4 is a block diagram of a variety of occupant sensing and health monitoring systems.

FIG. 4 is a block diagram of a variety of occupant sensing and health monitoring systems illustrating that various systems can be used together. As shown in FIG. 4, a respiration sensor 71 is used together with a heartbeat sensor 72, an optical sensor 73, a motion sensor 74, one or more weight sensors 75, a seatback angle sensor 76, one or more ultrasonic sensors 77 and a seat track sensor 78 (although only a subset of these sensors may be provided and/or used at any one time). These types of sensors are known sensors and any such sensors may be used in the invention.

Occupant motion can be determined by any of these technologies and need not be part of the electric field sensing system. Each of these sensors can feed into an ECU 79 which controls or interfaces with the airbag system 80 and the health and fatigue monitoring system 81. Alternative or additional sensors that provide information about the occupant may also be used in the invention. Thus, the airbag system 80 is controlled based on data obtained from the sensors. Various airbag system control techniques are envisioned, including those disclosed in patent publications mentioned herein.

Figure 5:
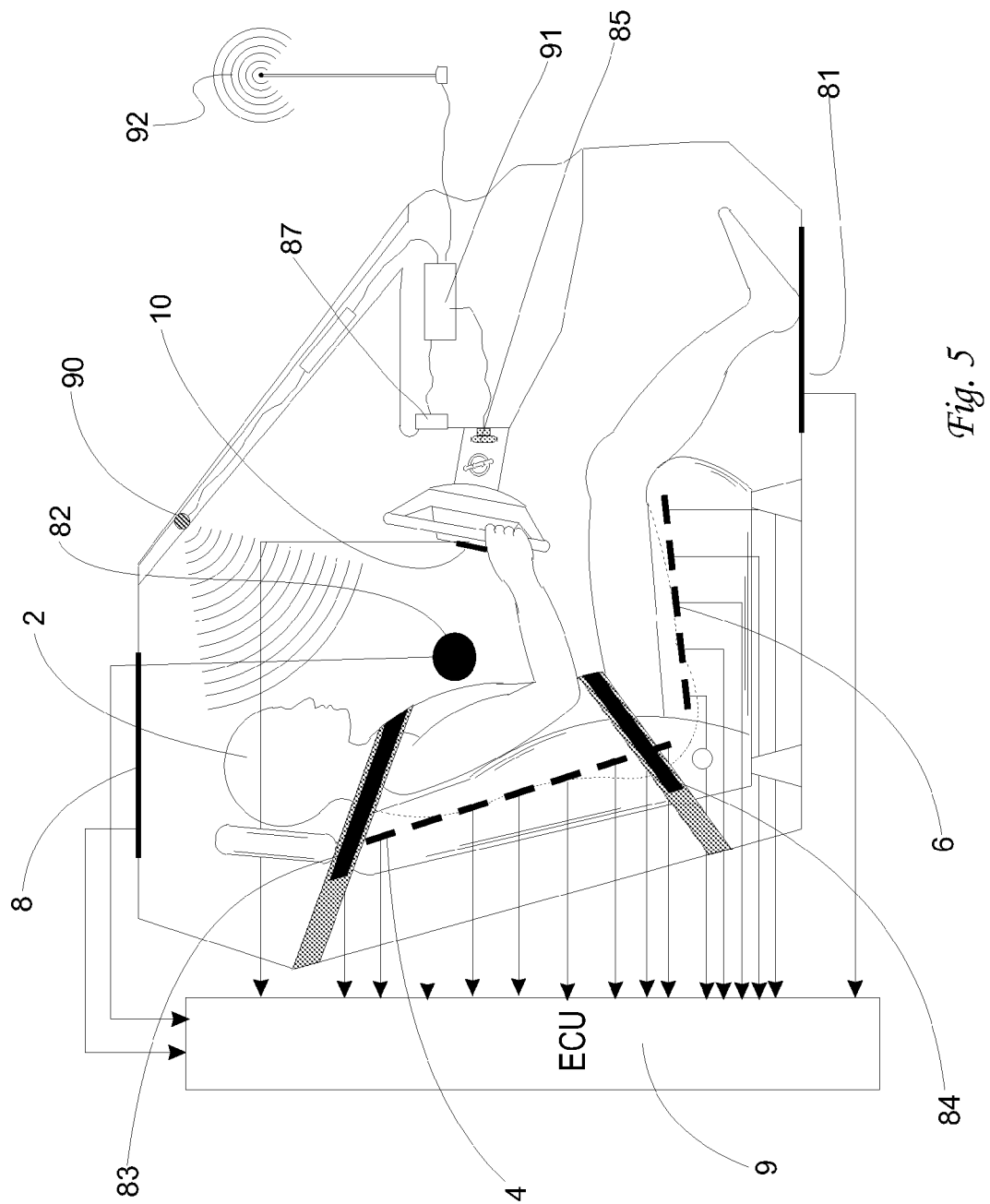
FIG. 5 is a side view, with certain portions removed or cut away, of a portion of the passenger compartment of a vehicle showing several preferred mounting locations of a driver health and fatigue monitoring system in accordance with a third embodiment of the invention.

FIG. 5 is a side view, with certain portions removed or cut away, of a portion of the passenger compartment of a vehicle showing several preferred mounting locations of a driver health and fatigue monitoring system and its various components. Several of the components are the same as illustrated and described above with regard to FIG. 1 and are numbered the same and will not be described again. Additional electric field antennas, each of which is coupled to the processor of the health and fatigue monitoring system with wires or wirelessly (ECU 9), include antenna 82 which is located in the side door alongside the driver's seating location and is useful when the driver is leaning more against the door than the seatback. Antenna 82 may represent one or more antennas. Each antenna 82 may be arranged in the door, i.e., between the panels defining the door, or on an inner side of the innermost panel.

Antenna 81, which can also be a set or group of one or more antennas, is located in the floor of the vehicle and is useful for monitoring motion of the driver. Each antenna 81 may be arranged on top of the floor pan in front of the driver's seat.

If the driver is instructed by the system to brake or slow the vehicle motion, and there is no motion of the driver's foot as determined by analysis of data from antenna 81, then the system may use this information along with other information to conclude that the driver is incapacitated, and possibly assume partial or total control of the vehicle or take other action (of the type described herein).

A key addition illustrated in FIG. 5 is the inclusion of antennas or antenna sets or groups 83 and 84 on and/or in the seatbelt, each antenna set or group 83, 84 including one or more antennas. An antenna on or in the seatbelt, if properly worn, can be the closest antenna to the lungs and heart and thus can provide the best heartbeat and respiration signals. More generally, each antenna group 83, 84 may be associated with the seatbelt so that one or more antennas thereof is (are) closer to the lungs and/or heart of the occupant. Antenna groups 83, 84 may be arranged on the seatbelt or woven into the material of the seatbelt and, in all cases, coupled through wires or wireless to the ECU 9.

In the event that the health and fatigue monitoring system determines that the driver is having a serious medical emergency, his or her life may be saved if the appropriate emergency personnel are notified. Also, in such a situation, it can be possible, depending on vehicle-resident equipment, for someone off the vehicle to assume control of the vehicle to avoid an accident. Communications antenna 92 is illustrated for that purpose. It is coupled to, e.g., via a wired connection, and can be controlled by the health monitoring system ECU 91. Communications antenna 92 is positioned anywhere on the vehicle in which it can receive wireless signals.

The health monitoring system ECU 91 can also receive information from the electric field monitoring system ECU 9, via a coupling or electrical connection therebetween (not shown), and notify the driver that the electric field monitoring system detects that he or she may no longer be capable of operating the vehicle and ask for feedback. A message to the driver can be in any form, such as a display, sound, light or any other system that can get the attention of the driver. The health monitoring system ECU 91 can also receive information from an occupant information providing sensor 90 mounted in the A-pillar, which sensor 90 may use waves (as represented) to enable a determination of information about the occupant (e.g., in the manner of ultrasonic sensors 77 described herein).

With respect to a sound message, in a preferred implementation, a recorded or synthesized voice can speak a message using speaker-microphone 87 to the driver and ask him or her to perform some task such as respond by saying a word or by depressing the horn or button 85 or performing a gesture such as raising his/her hand or pointing. The ECU 91 includes appropriate command circuitry (hardware/software) to enable the speaker-microphone 87 to generate the sound message, e.g., a message recorded in storage media at the speaker-microphone 87 or at the ECU 91.

A time delay between the message and the action by the driver can be a good indication of the driver's condition. This time delay is computed by a processor in, for example, the health monitoring system ECU 91 that is provided with the time at which the message is conveyed to the driver via the speaker-microphone 87 or other device, and the time at which the driver provides the requested response thereto.

In some installations, it can be desirable to test and score the driver's reaction when he/she starts the vehicle. The health monitoring system can ask one or more times for a response, as above, from the driver in order to determine the alert response time of the driver and to train the driver as to what to expect so that he/she is not surprised at a later time. In some cases, this initial test can determine that the driver is not fit to drive the vehicle and prevent him/her from doing so (via any vehicle operation suppression system known to those skilled in the art including any of these described herein). If the driver is the vehicle owner, then he/she should be familiar with the operation of this system and if he/she responds differently than at some previous time, then again vehicle operation can be suppressed.

FIGS. 6A-6C illustrate the principles of operation of a single electric field monitoring element in the presence of a body element and a modified body element, which principles may be used in any of the embodiments of the invention herein. FIG. 6A illustrates the case where there is no body element to affect the electric field and thus current i1 is the resulting current in the circuit. Oscillator 101 provides the electric field to the antenna 100. When a body element 103 is placed in the electric field, a different current i2 results as shown in FIG. 6B. Finally, when the body element 103 changes shape, for example as illustrated by 104 in FIG. 6C, a still different current i3 results. When a driver is breathing, his effect on the electric field changes as he breathes and thus there will be a cyclic variation in i2-i3 which corresponds or can be related to his respiration rate. If he/she suddenly stops breathing, as might happen during a heart attack, the cyclic variation will stop and this can be determined by monitoring the variation in the current in the antenna circuit, i.e., by a current monitor that is known to those skilled in, for example, the electrical art. In a similar manner, the heartbeat can be monitored. Finally, in the case where only the heartbeat is monitored, the respiration signal can be derived from the heartbeat signal. This is further made possible since the heartbeat frequency is substantially higher than the respiration frequency and thus the two signals can be readily separated by signal processing techniques that are well known to those skilled in the art.

In a similar manner, FIGS. 7A-7C illustrate principles of operation of a pair of interacting electric field monitoring elements in the presence of a body element and a modified body element. In this case, two antennas are selected which are those that are best able to monitor the heartbeat or respiration rates. Again, the effect of breathing or the beating heart is to change dielectric properties of the body element and thus the current in the antenna circuit, i.e., from i4 wherein there is no body element (FIG. 7A), to i5 wherein the body element 103 is placed into the electric field between the two antennas (FIG. 7B), to i6 wherein the body element 103 changes shape to 104 (FIG. 7C).

Figure 8:
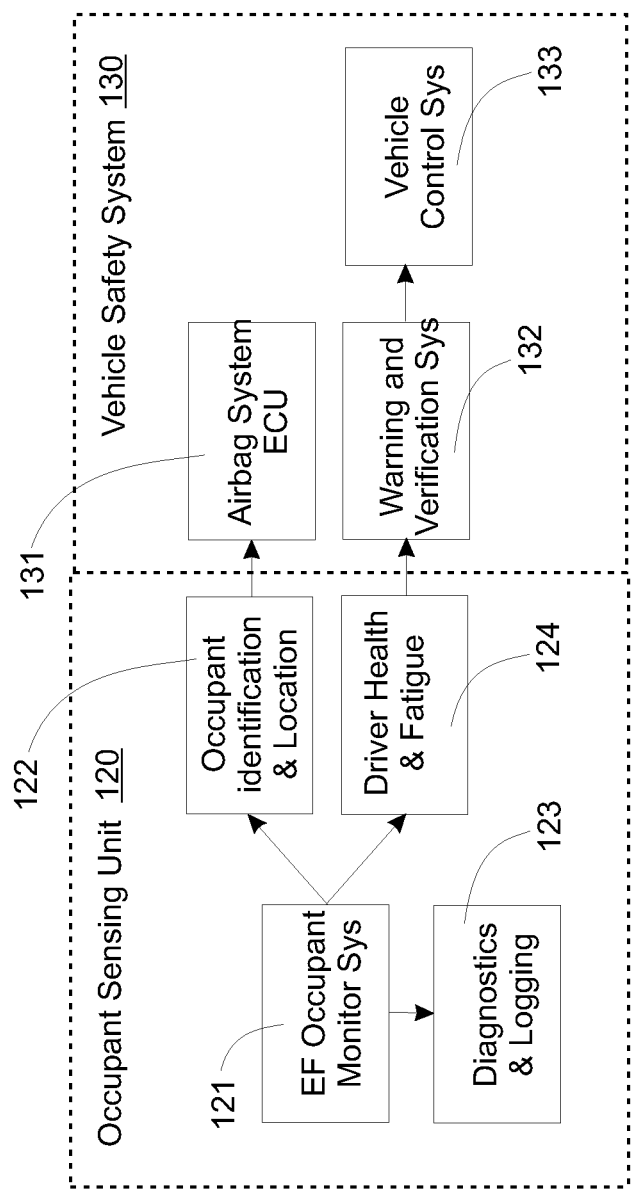
FIG. 8 is a block diagram illustrating the relationship between the occupant sensing unit and the vehicle safety system in accordance with the invention.

A block diagram illustrating one possible relationship between an occupant sensing unit 120 and a vehicle safety system 130 is illustrated in FIG. 8. An electric field monitoring system 121 is connected to a diagnostics and data logging module 123 which verifies that the system 121 is operational and logs any error codes. Electric field monitoring system 121 can also log particular characteristics of a particular driver if a set of individual preferences are identified and associated with the normal drivers of the vehicle. Logging of error codes and particular characteristics of an identified driver may be performed in a manner known to those skilled in the art, with the logged data being stored in storage medium accessible by a processor.

In this manner, the electric field monitoring system 121 would know what the normal heartbeat rate and respiration rate of driver 1 is and can then better identify anomalies as they occur, once the driver is identified by accessing the logged data previously entered into the storage medium. Such a driver, for example, may have a history of skipping beats and it must be known that this should not be a concern of the health monitoring system, unless the rate of skipped beats increases which can be attributed to a potential medical problem, alcohol or drug abuse. Such a system may also be used as a biometric measure to identify the driver along with normal heartbeat rate and respiration rate, for example.

Electric field monitoring system 121 also provides data for the passenger occupant identification and location system 122, the conventional use of electric field sensors, and the driver health and fatigue monitoring system 124 (see FIG. 8). Occupant identification and location system 122 connects with the vehicle airbag system 131 and controls the vehicle airbag system 131, such control being variable and including causing inflation or deployment of one or more airbags in the airbag system 131 to be suppressed for a rear-facing child seat, for example.

Driver health and fatigue monitoring system 124 similarly connects to a vehicle warning and verification system 132 which tests the driver to see whether he is capable of operating the vehicle and if not, control of the vehicle can be taken over by a vehicle control system 133.

Figure 9:
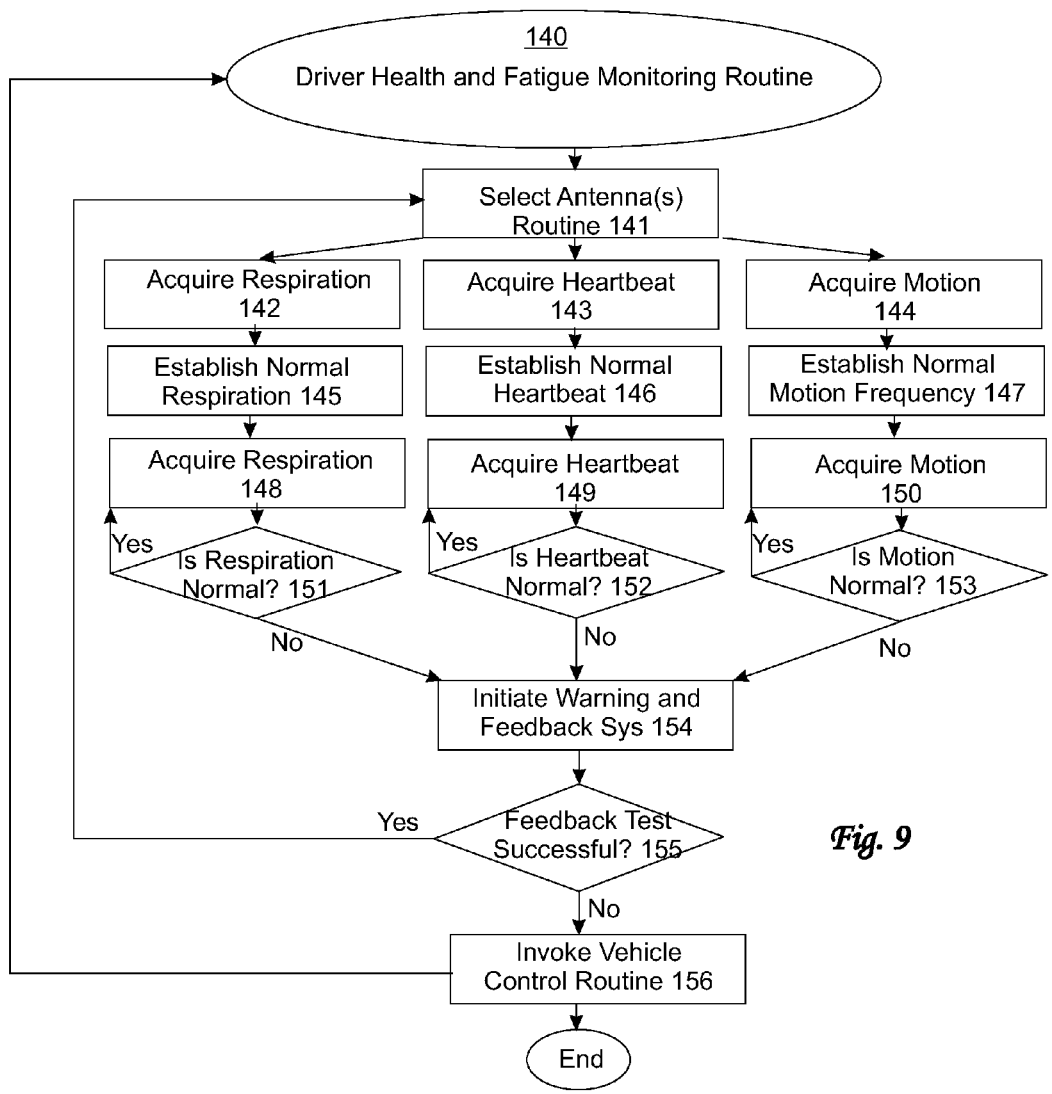
FIG. 9 is a flow chart showing the operation of the driver health and fatigue monitoring routine in accordance with the invention.

An exemplifying, non-limiting flow chart showing the operation of the driver health and fatigue monitoring routine, for any of the embodiments described herein, is shown in FIG. 9. The routine is illustrated generally at 140 and when invoked, starts the select antenna routine 141 which surveys all, or a subset, of the various antenna scenarios, including each one individually and then in pairs. Select antenna routine 141 will look for the strongest antenna signals for heartbeat, respiration rate and occupant motion. Once selected, control passes to the modules that acquire respiration 142, acquire heartbeat 143, and acquire motion 144 and establish or record normal respiration 145, normal heartbeat 146, and normal motion frequency 147, what will be termed the established respiration rate, heartbeat rate and typical occupant motion.

The time periods for each of these functions will often differ significantly. Less than one minute is generally sufficient to establish a representative heartbeat rate, several minutes is generally sufficient to establish a representative respiration rate and a longer time may be needed to establish how the particular driver typically moves while operating the vehicle. Establishment of a normal motion is the least important of the three since it will mainly become important when an anomaly has been detected in the heartbeat or respiration rates. If the driver has stopped his normal motion when there is a significant heartbeat event, then this may confirm that there may be a problem with the driver, rather than a failure of the electric field monitoring system 121. Also, significant motion may be a clue that the select antenna routine 141 requires reactivation. Thereafter, the respiration, heartbeat and motion are acquired at 148, 149, 150, respectively.

Steps 151, 152 and 153 determine whether any of the measured heartbeat, respiration and motion rates are normal and if not, i.e., if one is not normal, a warning and feedback system is invoked or activated at 154. If the driver fails a feedback test generated by the warning and feedback system, step 155, then a routine to control the vehicle is invoked or activated at 156. The vehicle control routine that is invoked at step 156 may involve, for example, signaling to a remote site or facility for attempted driver communication and then for exercising vehicle control provided there is sufficient equipment on the vehicle to allow the remote operator to observe the driving conditions, traffic, etc. and thus permit a remote operator to slow the vehicle and guide it off onto a shoulder. Since, in most cases, this will not be possible, sufficient apparatus must be on the vehicle to permit this routine to flash emergency lights, sound the horn and/or bring the vehicle to a safe stop. At this point, the routine can optionally contact the proper authorities so that someone is dispatched to the vehicle.

The vehicle control routine 156 may also be performed partly or entirely by equipment on the vehicle upon command by a software program that is executed when needed. The equipment necessary for the control unit to invoke control of the vehicle includes, but is not limited to, devices that are coupled to the steering wheel or steering system, the brakes or braking system, the throttle system, transmission and/or engine. These devices may be controlled by software to reduce the speed of the vehicle to a stop and direct the vehicle to a safe area, e.g., the side or shoulder of a road. The vehicle control routine 156 may therefore correspond to or encompass a processor and control equipment that is coupled to vehicular parts that affect operation of the vehicle, e.g., the brakes, steering wheel and throttle, and possibly servos or actuators therefor. The manner in which this structure operates to effect vehicular control would be easily understood by those skilled in the automotive art in view of the disclosure herein.

Although not illustrated in the flow chart, the presence and characteristics of the heartbeats of vehicle occupants can be valuable information that can and should be communicated by the communications unit to EMS personnel as part of the automatic collision notification message, if it is available. Therefore, the EMS personnel will know whether the occupants are alive and some indication as to their health state. This may be effected using a communication system or a transmission system on the vehicle (not shown) that is coupled to the vehicle safety system 130, or a part thereof, and obtains and transmits the information about the occupant(s) of the vehicle. The transmission may be accompanied by a location of the vehicle, obtained using a location determining system on the vehicle or apart from the vehicle, and may be effected using any known communications protocol, including using the Internet.

Figure 10:
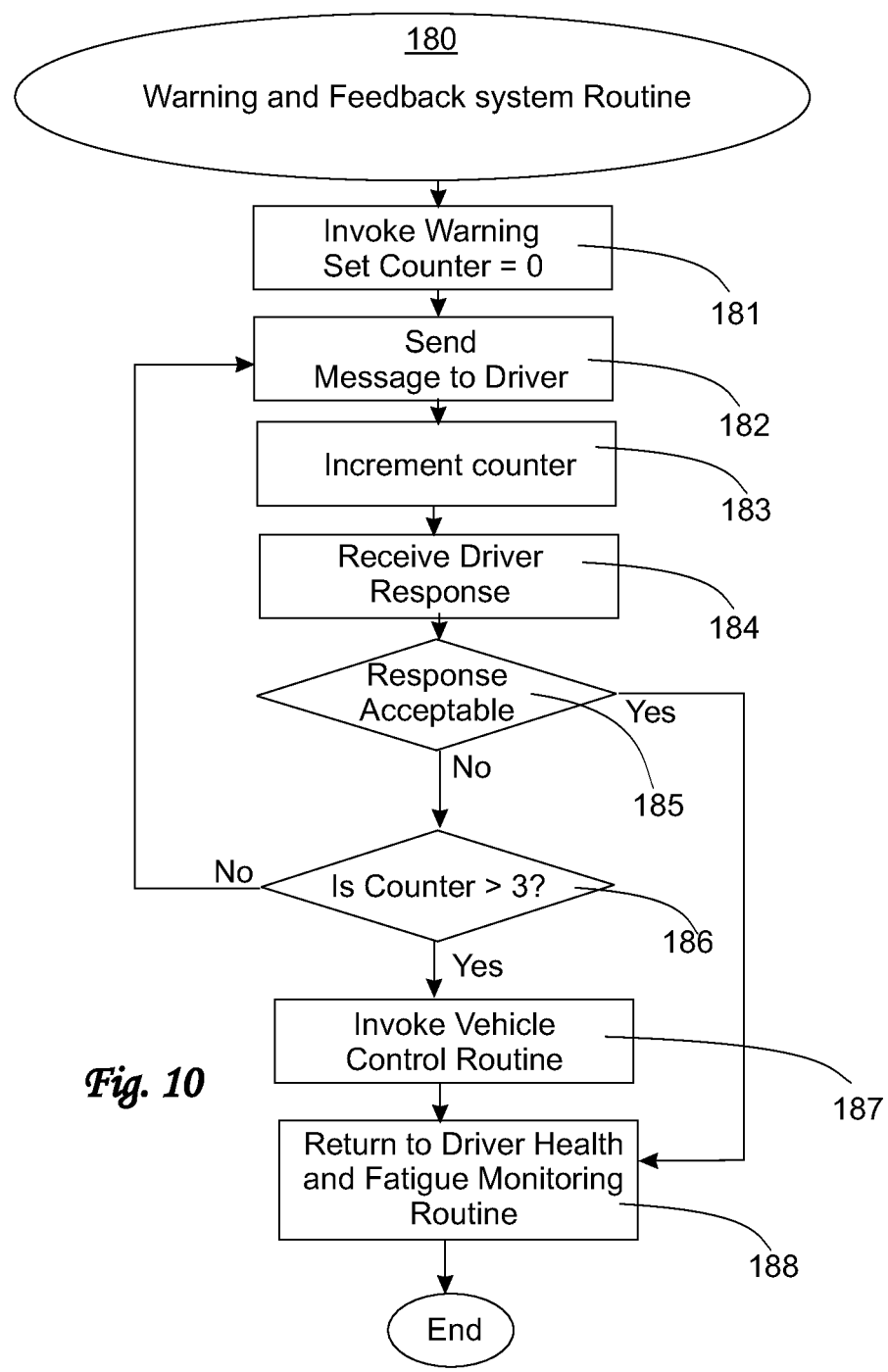
FIG. 10 is a flow chart showing the operation of the warning and feedback system routine in accordance with the invention.

An exemplifying, non-limiting flow chart showing the operation of an exemplifying, non-limiting warning and feedback system routine, for any of the embodiments described herein, is shown in FIG. 10. The routine is illustrated generally at 180. A first step in the routine 180, at 181, is to initiate a warning set counter. The second step 182 is to generate and send a message in some form to get the attention of the driver. This message can be in any of several forms, e.g., audible, visual, tactile, such as a warning buzzer or a flashing light which can suffice, but this may confuse a driver that is unfamiliar with the system. If the vehicle is equipped with a heads-up display or other display that will get the attention of an alert driver, then a message can be displayed on one or more of such displays. A preferred message is to have a synthesized or recorded voice announce a message to the driver. A combination of the above warnings can be better still. The message can instruct the driver to take some deliberate action which will not interfere with his ability to operate the vehicle but will nevertheless indicate that he has received the message and responded in a timely manner.

Another display that can be used when sufficient data is available is a light or other visual display that shows or otherwise depicts the calculated awake state of the driver. A driver can monitor this display and get an indication as to whether the system thinks that he/she is falling asleep or otherwise experiencing a decrease in his/her ability to operate the vehicle. A driver that sees that he/she is gradually becoming drowsy can, and will ideally, plan when to stop and rest or get a cup of coffee. Also if the driver is sure that the system is in error, he/she can provide feedback to the system that can be taken into account to improve the system accuracy. One candidate device is the Ambient Orb from Ambient Devices, Cambridge, Mass. which is programmed to change color based upon the output of a state detection system.

After the message is sent to the driver at step 182, the counter is incremented at 183 and the system waits for a response at 184. If the response is not the expected response or if it is tardy (tardiness being determined relative to a predetermined time threshold that may be a function of, for example, the message or the current situation), then the response is judged to not be acceptable at step 185. If the response is judged acceptable, then control is passed back to the health monitoring routine at step 188. The count of the counter is checked at step 186 after an unacceptable driver response and if the counter exceeds some predetermined limit, such as three, then the vehicle control routine is invoked at step 187. If the counter is below its limit, then control is passed to step 182 and the driver is given another chance to respond to the message. As shown in FIG. 10, the routine returns to step 182 to send a message to the driver. However, if the message is a continuous message, such as one on a display, then the routine could be programmed to return to the increment counter step 183 (see the dotted line in FIG. 10).

Since the situation can be life threatening, it is important to provide only a limited amount of time for the driver to react to the message (the receive driver response step at 184). In the case of a drowsy driver, the system can also provide some advice, especially after a number of detected abnormalities that perhaps the driver should take a break. If the driver does not take the advice and there is a likelihood that the driver will in fact fall asleep, then the authorities can be notified. Such notification may be additional or alternative to the invoke vehicle control routine 187, see step 189 in FIG. 10. This notification may be provided by a communications system or transmission system (not shown in FIG. 10) that is coupled to the electric field monitoring system 121 and generates and sends an appropriate message relating to the lack of the driver providing a response for the predetermined amount of time to the sent message.

Another feedback system that has been suggested is to provide some change in vehicle operation that requires a driver response and then measure the response time. One such idea is to perturb the steering wheel either with a pulse or with a gradual drift of the vehicle to one side of the road and then measure how quickly and even if the driver makes a response.

2. Optical Driver Health Monitoring

Figure 11A:
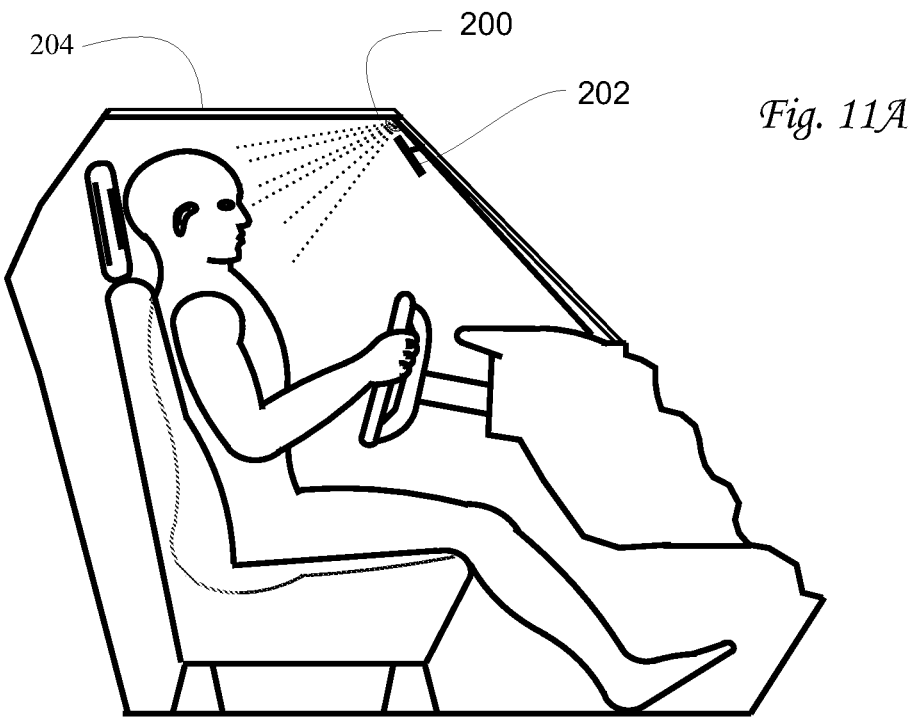
FIG. 11A is a view of an optical monitoring system in accordance with the invention that monitors a portion of the face of the driver from an imager mounted near the top of the windshield with an alternate mounting location on the rear view mirror.

FIG. 11A is a view of an optical monitoring system that monitors the face of the driver from a camera and illumination system 200 mounted on or near a ceiling 204. One preferred location, for example, is on or adjacent to the rear view mirror 202 (schematically illustrated) since that location usually has a good view of the driver's face and is not obstructed by the visor. The optical monitoring system comprises a camera and a source of illumination which is usually in the non-visible part of the electromagnetic spectrum and in particular in the infrared (IR) portion of the electromagnetic spectrum. The optical monitoring system also comprises a processor or processing unit coupled to the camera, and optionally the illumination source. This processor is configured to analyze the images to obtain information or data therefrom, and specifically, from images of blood vessels, capillaries and veins in a face of the occupant being imaged.

Blood, in particular, reflects in the IR portion of the spectrum and thus permits a clearer image of the blood in the blood vessels, capillaries and veins in the driver's face to be obtained and visible in the images being obtained by the camera. Pulsations of the blood flow can then be used to measure the heartbeat rate of the driver. In particular, the heartbeat variability can be analyzed by the processor as this permits a determination of the drowsiness and/or other attributes of the driver. This is discussed below in the analysis section.

Another use of this technology is to use the pattern of blood vessels, capillaries and veins in the driver's face as a biometric identifier of the driver.

If the camera is sensitive to longer wave IR, or if a separate imager is used, the temperature of the driver's face or portions thereof can also be measured by a temperature measurement device or algorithm and compared to ambient temperature as measured by a temperature sensor to determine whether the driver's temperature is normal or indicative of a medical problem. The overall motion of the driver's face can also be tracked by the processor, e.g., using a tracking algorithm or under control or command of software available to the processor, to determine the respiration rate of the driver. The face location can be determined in the images using, for example, pattern recognition techniques operated by the processor. Finally, the degree to which the blood capillaries, vessels or veins change in size during a beat or their absolute size, as determined by the processor, can provide a measure of the driver's blood pressure.

In addition to near and far IR illumination, the pulse rate has been found to be best determined from the green part of the optical spectrum. Since blood is particularly absorbent of frequencies in the 500 nm to 600 nm range, the illumination can contain frequencies in this range. Since green light can be distracting to the driver and vehicle occupants, care must be exercised as to how it is used. Once the driver's face location has been determined by appropriate analysis software embodied on computer-readable media that is executed by the processor, a patch on the forehead, cheek, neck or other convenient place can be chosen as the spot to be illuminated. Then, the amount of illumination can be adjusted, via control of the source of illumination by the processor or control unit more generally, so that it is barely above, typically 1% to 10% above, that present in the ambient light level. Finally, it can be carefully focused so that it doesn't spill over and illuminate the eyes of the driver. The location of the source of illumination should also be carefully chosen so that reflections do not strike the eyes of other vehicle passengers. Multiple sources of illumination may be also provided and used independently or in combination to ensure the selected spot can always be illuminated.

The green light can also be modulated, via a modulation device or technique, so that it can be separated from ambient light reflections. This may require that the receiving device for the green light be a photodiode or equivalent to permit the modulations to be sensed and separated from the ambient light.

It has been found by several investigators that since the green frequencies, particularly at 540 nm and 580 nm, are the most absorbed, the variations in reflected light are greatest and thus the variations in blood flow rate most easily identified and measured from light in this frequency range.

Once the camera, processor and processing software has chosen a spot to monitor on the driver's face, it is extremely beneficial to track this spot over time. Techniques for accomplishing this tracking are discussed in the Borgobello paper referenced above and in other publications by MIT on this subject, all of which may be used in the invention.

Camera and illumination system 200 can also be used to track the eye and eyelid motions of the driver as is discussed in prior art eye tracking systems for determining driver alertness. As mentioned above, such systems can be used to augment the monitoring system discussed herein but, when relied on alone, suffer from problems associated with sunglasses and even ordinary glasses which frequently block IR.

Figure 11B:
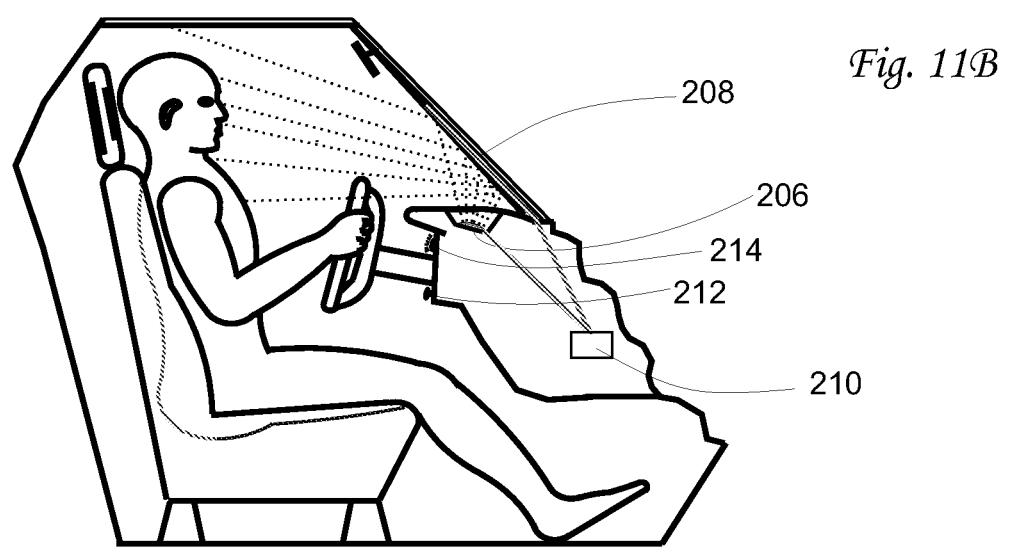
FIG. 11B is a view of another embodiment of an optical monitoring system in accordance with the invention that monitors a portion of the face of the driver from an imager mounted in the instrument panel facing so that it reflects off a portion of the windshield.

FIG. 11B illustrates an alternate arrangement for monitoring the face of a driver. In this implementation, a camera 206 is mounted below the top surface of the instrument panel in such a position as to view the driver's face through a reflection off of a surface 208 of the windshield in a manner similar to heads-up displays. This implementation has the advantage that a larger camera can be used with greater resolution and can contain focusing hardware and even pointing hardware under control of an ECU 210 to obtain a better view of the face of the driver and to more exactly project the artificial illumination and particularly the patch of green light discussed above. This patch projection will move as the driver's head moves, under control of a processor and appropriate control algorithm or program in the ECU 210. In both cases, an alternate approach is to illuminate a significant portion of the driver's face with the green light but to do so at a level slightly above the ambient green light level and use more care in separating it from the ambient reflections. Otherwise, the operation in FIG. 11B is similar to that of FIG. 11A. The same ECU 210 can be used to analyze the driver for signs of fatigue and initiate a warning such as a light 214 which requires a feedback response from the driver, such as depressing button 212, speaking a word, pointing etc as described above.

In many cases, it is desirable to displace the illumination source from the receiver which can make variations in blood flow more observable.

There are a number or additional monitoring methods that can yield important information about the health and status of the vehicle driver. A few of these will now be mentioned but many others appear in the medical literature on patient monitoring.

There is some indication that the presence of alcohol and/or drugs in the blood can be detected by the reflectance of certain IR frequencies off of the face particularly for alcohol in the wavelength range between 1600 nm and 1900 nm. Since various such substances can be emitted from the skin, illumination at the proper frequency can cause an unusual absorption of the incident light compared with that of a close but non-absorbed wavelength.

Temperature variations, particularly near the nostrils, can be monitored to yield the respiratory cycle. Thermal face measurements can also provide evidence of inebriation or drug use that can impair the driver's ability to operate the vehicle safely.

As mentioned above, the monitoring of sudden head motion can indicate an attempt by the driver to wake from a micro-sleep.

If the illumination with green light is not used, the area adjacent the eyes can exhibit pulsation corresponding to the heartbeat.

As reported "Eye-Activity Measures of Fatigue and Napping as a Fatigue Countermeasure", a TRB TechBrief accession Number 00763223 May 6, 1999 (ntl.bts.gov/lib/21000/21700/21706/PB99134900.pdf), there are at least six optical clues to drowsiness that can be used in combination with the heartbeat and respiration methods described here. There are:

1. Blink duration measures derived from an eye tracker
   Blink closing duration was found to be longer in the minute preceding off-road accidents than immediately after, and considerably longer than just before or at the start of driving.
2. Blink frequency effects that were similar to those of blink duration. However, the results with blink frequency were less consistent than with blink duration.
3. Partial eye closures during fixations, measured as the ratio of vertical to horizontal pupil diameter (V/H) show this parameter is particularly impressive as an indicator of degraded alertness at least 2 to 3 minutes before an accident and likely as much as 10 to 12 minutes before an accident.

4. Eye closures occurred with a relatively high frequency in the minute preceding off-road accidents and showed a dramatic increase starting 20 to 30 seconds before accidents.

5. Saccade frequency (rapid eye movements) was markedly higher in the 30 seconds following as compared to the 60 seconds preceding off-road accidents.

6. Large head and body movements were observed as being obvious indicators of fatigue.

A number of these can only be accurately determined through the use of special equipment that was available on the driving simulator where these tests were made.

In another study, the respiration wave form was accurately determined for several people from a distance of 6-8 feet indicating that video monitoring with the appropriate illumination can measure respiration. Thus, monitoring of the driver's chest can augment facial monitoring for determination respiration.

Major arteries in the neck can be used to measure heartbeats through thermal imaging if these are visible to the thermal imaging system. This becomes problematic when the driver is wearing a winter coat or sweater which covers these arteries.

Another approach is to simultaneously monitor the gaze direction of the driver and the events occurring in the space surrounding the vehicle. If such an event catches the attention of the driver, then the speed of his/her reaction can be measured as an indicator of inattention. If the driver misses a series of events that he/she should not have missed, then this can be a dramatic indication of inattention and the driver should be tested.

The volume of air coming from the nostrils is measured in accordance with apparatus and techniques disclosed in U.S. Pat. No. 5,689,241 to determine whether the person is getting enough oxygen. If not, then drowsiness can quickly result. This is known as hypoventilation. This can be done using far IR illumination in the 6-15 μm wavelength range.

3. Weight-Based Driver Health Monitoring

Figure 12A:
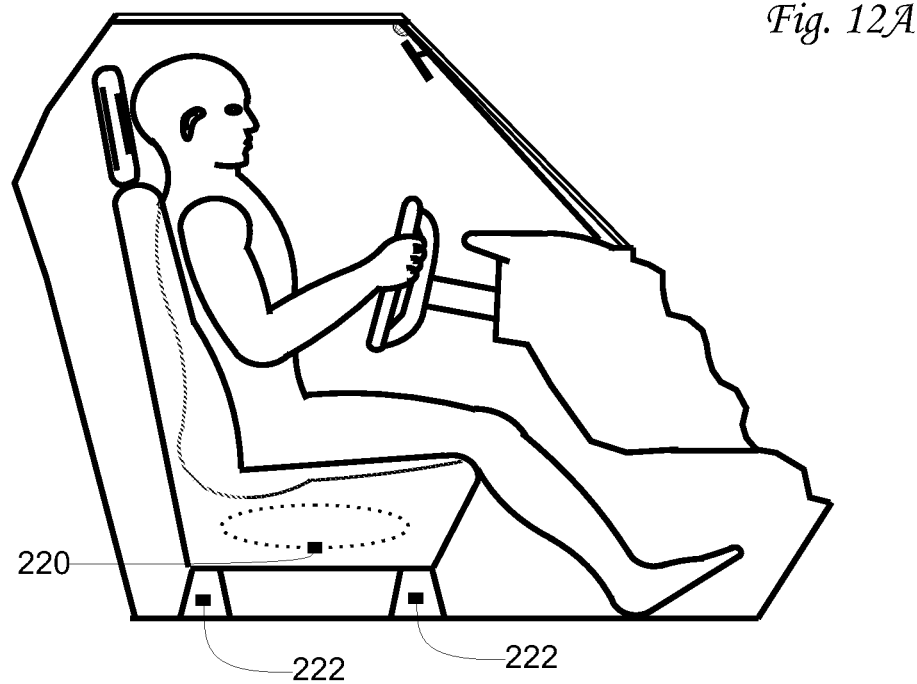
FIG. 12A shows a seated-state detecting unit along with an optical sensor, a weight sensor, a reclining angle detecting sensor, a seat track position detecting sensor, with a heartbeat, respiration rate and motion sensor as part of an bladder weight sensor, for use in any of the embodiments of the invention.
Figure 12B:
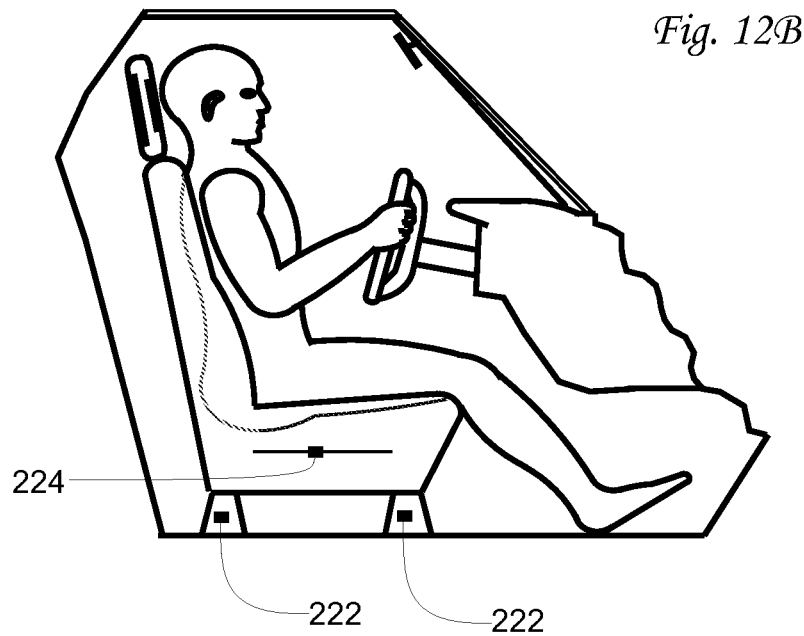
FIG. 12B is an illustration as in FIG. 12A with the replacement of the bladder weight sensor of FIG. 12A by a strain gage or displacement weight sensor within a cavity in the seat cushion and on the seat support structure, for use in any of the embodiments of the invention.

A variety of different sensors that also have some capability of measuring the heartbeat and/or respiration rate, or contributing the determination of the heartbeat and/or respiration rates, as well as gross movement of the driver are shown in FIGS. 12A and 12B. These sensors can be used in combination with the systems disclosed elsewhere herein or independent therefrom.

A bladder weight sensor 220 in the seat bottom cushion as well as two strain gage weight sensors 222 on the seat support structure are shown in FIG. 12A and described in U.S. Pat. No. 7,779,956 and patents and applications related thereto. In addition to or in place of strain gage weight sensors 222, a strain gage weight sensor 224 can be positioned within the seat bottom cushion (see FIG. 12B) in such a manner so that it also can measure the heartbeat and respiration rates of the driver although not as accurately as the electric field or optical sensors discussed elsewhere herein.

Many practical problems have arisen during the development stages of bladder and strain gage-based weight systems. Some of these problems relate to bladder sensors and in particular to gas-filled bladder sensors and are effectively dealt with in U.S. Pat. Nos. 5,918,696, 5,927,427, 5,957,491, 5,979,585, 5,984,349, 6,021,863, 6,056,079, 6,076,853, 6,260,879 and 6,286,861. Other problems relate to seatbelt usage and to unanticipated stresses and strains that occur in seat mounting structures. These problems relate more to the use of these devices as weight-based occupant sensors and have little effect on the use of these devices as health monitors.

Fluid-filled pads have been used for detecting heartbeat and respiratory motions in patients and infants but not to vehicle operators or passengers as reported in U.S. Pat. Nos. 5,515,865, 5,684,460 and 5,853,005. Use of strain gages for heartbeat and respiration measurements to determine the presence and classification of an occupant is disclosed in U.S. Pat. No. 7,019,641; however, there is no disclosure as to how to use the invention to detect drowsiness.

4. Seat Mat Local Displacement Monitoring

Another method of monitoring the heartbeat of an occupant of a vehicle is to make use of a local relative displacement measuring seat mat. This device can be implemented in several versions with the preferred version comprising a grid of small cells which can be from a few millimeters to a centimeter is size and where for each cell the displacement of the top surface relative to the bottom surface can be monitored using, for example, capacitance. The heartbeat is detectable in several large veins or arteries in the butt of the occupant and this causes relative displacement of the tops of several cells toward the bottoms. If both the top and bottom of each cell is conductive then the capacitance changes which can be measured. If the bottom of each cell is connected through horizontal conductors and the tops through lateral conductors, each cell can be individually interrogated to determine its capacitance. The tops and bottoms of the cells can be held separate from each other through metal or other springs or through compressible fluid as, for example, in BubblePak®. This technique can be used to determine the heartbeat rate independently of the heartbeat rate as determined by other systems or techniques disclosed herein, or to verify the heartbeat rate as determined by one of the other systems techniques disclosed herein, or vice versa.

5. Other Systems for Driver Health Monitoring

Use of radar for the monitoring of heartbeats was first disclosed in one or more of the current assignee's patents or patent applications. Analysis of heartbeat and respiration rates to determine drowsiness in vehicle drivers is believed to be first disclosed herein. Heartbeats and respiration can be determined by radar and appropriately analyzed as discussed elsewhere herein to assess the state of driver or other occupant drowsiness and one novel method would be to place the radar device in the seatbelt where it has a good view of the heart and chest of the occupant. Radar devices are now available as an electronics chip and thus one or more such chips can be easily and unobtrusively incorporated in a seatbelt. Another preferred location is in the steering wheel; however, care must be exerted to see that it is properly aimed at the chest in spite of driver's preferences.

Ultra wide band (UWB) radar is particularly appropriate for this application. This is also reported more recently for use in medicine in "UWB radars in medicine", Staderini, E. M., Aerospace and Electronic Systems Magazine, IEEE, January 2002 Volume: 17 Issue: 1, On pages 13-18. The radar vital signs monitor disclosed therein is able to measure the subject's heartbeat and respiration rate at a distance up to 30 feet. "Non-Contact Measurement of Heart And Respiration Rates With A Single-Chip Microwave Doppler Radar", Amy Diane Droitcour, PhD Dissertation Stanford University, June 2006, discloses the availability of such radars on a chip. In another reference, heart rate variability was measured using 35 GHz radar where the resolution on the order of 0.1 mm was achieved for monitoring heart motion. Finally, U.S. Pat. No. 7,196,629 discloses a radar mounted on the steering wheel for monitoring of heartbeat and respiration but the patent is silent as to how this information is used to determine driver drowsiness.

Another approach for measuring heartbeats and respiration is to place an accelerometer in the driver's seatbelt or even in the seatback. Sensitive accelerometers are capable of yielding signals from which the heartbeats and respiration can be measured. This is partially disclosed in U.S. Pat. No. 6,011,477 for the monitoring of infants. It is even possible to place accelerometers in the seat bottom for the same purpose with significant noise problems caused by vehicle motion.

Direct measurement of EEG emissions from the head of the driver can, in principle, be done in a non-contact manner as disclosed in U.S. Pat. Appln. Publ. No. 20080015801; however, the equipment disclosed in very bulky and expensive and thus not suitable for in-vehicle monitoring. EEG signals are probably the most reliable in determining the onset of sleep so, as this equipment is improved, it may become available for in-vehicle use. Also the SmartCap discloses a cap that can monitor brain emissions as a sort of EEG as disclosed above.

6. Analysis Methods for Driver Health Monitoring

An important part of the determination of driver drowsiness is in the analysis of the heartbeats and respiration. Looking at the heartbeat rate alone, one can say that if the rate is too high, the driver may be having a seizure or other perhaps critical health problem. If it is too low, this too can indicate a serious medical problem or that the driver is under the influence of drugs or alcohol. An irregular rate may indicate a heart attack, stroke or tachycardia event. Although a low heart rate may indicate that the driver is asleep, this is not always the case and by the time that it is detected, it may be too late.

Similarly, when the respiration rate is too high, a seizure or other serious medical problem may be in progress. Too low of a respiration rate may indicate sleep, alcohol or drugs and an irregular rate may indicate suffocation, a heart attack, stroke or other medical problem. Again, by the time that it is detected, it is usually too late to prevent an accident.

A key to getting the most information from the heartbeat rate and in sufficient time to warn the driver or take other action lies in its variability over time. This is known by the acronym HRV for heart rate variability. HRV is a measure of the oscillation of the interval between consecutive heartbeats. The literature is replete with references to this measure that are expressed in terms of consecutive cardiac cycles. Such terms include: cycle length variability, heart period variability, R-R interval variability (referring to the beat-to-beat interval formed by consecutive R-waves of the cardiac signal), and the R-R interval tachogram. The spectral components of the cardiac interval signal for short-term changes in HRV fall into three frequency ranges: the Very Low Frequency (VLF) range, the Low Frequency (LF) range, and the High Frequency (HF) range. For long-term changes in HRV, e.g., 24 hour recordings, the Ultra Low Frequency (ULF) range is also examined.

The LF component, known as the baroreflex band, is of chief interest as an indicator of cognitive workload. This component, commonly referred to as the 0.10 Hz component, reflects short-term changes in blood pressure and spans a range from 0.04-0.15 Hz. That is, there are approximately 6 fluctuations of the heart per minute due to changes in blood pressure. A peak in this component is indicative of lower cognitive workload conditions. A flattening of this component reflects conditions of greater mental workload. Other influencers of HRV include smoking and the acute ingestion of alcohol both of which reduce HRV.

While HRV of the ATC (air traffic control) experienced population appeared to decrease consistently with increases in the number of free flyers in the environment (an indication of an increase in mental effort), the increase from 12 to 16 free flyers resulted in an increase in HRV. This points to the potential use of HRV as an indicator of the point at which the capacity of human resources to process the increased number of free flying targets is being exceeded. It has been found that when tasks become too difficult there is a tendency for humans to disengage from the task resulting in an increase in HRV. See, "Heart Rate Variability: Indicator of User State as an Aid to Human-Computer Interaction", Rowe, D. W., Sibert, J., Irwin, D., CHI '98 Proceedings of the SIGCHI conference on Human factors in computing systems.

CHF (chronic heart failure) is associated with autonomic dysfunction, which can be quantified by measuring HRV. A reduction in SDNN (Standard deviation of the time between beats) identifies patients at high risk of death and is a better predictor of death due to progressive heart failure than other conventional clinical measurements. This is reported in "Prospective Study of Heart Rate Variability and Mortality in Chronic Heart Failure: Results of the United Kingdom Heart Failure Evaluation and Assessment of Risk Trial (UK-Heart)" James Nolan, Phillip D. Batin, Richard Andrews, Steven J. Lindsay, Paul Brooksby, Michael Mullen, Wazir Baig, Andrew D. Flapan, Alan Cowley, Robin J. Prescott, James M. M. Neilson and Keith A. A. Fox, Circulation 1998; 98; 1510-1516. Generally, an irregular pulse rate can indicate cardiac abnormality which may or may not be serious. If this occurs suddenly and does not go away, the driver should be warned and the system should be prepared for the need to assume control of the vehicle.

In the resting or baseline state, the heart rate will fluctuate with the breathing cycle; inspiration is accompanied by heart rate elevation and expiration is accompanied by heart rate depression. Thus, the respiration cycle can be determined from the heart rate, although it is more accurately determined by direct measurements. In some of the systems disclosed herein, only the heartbeats are measured and thus the respiration cycles must be determined from the heart beat cycles.

Heart Rate Variability in the VLF range decreases consistently and significantly minutes before falling asleep events. The sympatho-vagal balance is very low compared to baseline wake values for about 5 minutes before the events. The mean heart rate and overall HRV decrease during falling asleep events by 2.2 standard deviations (SD) and 2.9 SD below regional means. These changes found during wakefulness test suggest that ECG derived parameters in the time and time-frequency domains may provide a useful tool for monitoring drivers' drowsiness and preventing traffic accidents. (See, "Early Detection of Falling asleep at the Wheel: A Heart Rate Variability approach", G. Dorfman Furman, A Baharav C. Cahan, S. Akselrod, Computers in Cardiology 2008; 35:1109-1112.) This study was done using a driving simulator where the volunteer drivers remained connected to EEG, EMG, EOG, and ECG with continuous audio-video recording during the entire testing time. Since this is not feasible for application to production vehicles, the techniques of using electric fields, optics and/or the other systems discussed herein are thus needed to obtain the heart variability information to monitor the driver's HRV.

Changes in the autonomic regulation of the cardiovascular function occur in preparation for normal sleep and also when a person faces different tasks. Looking into these changes through the window of HRV, with a special focus on falling asleep at the wheel, sleep deprivation was employed as a means to increase the propensity to fall asleep. Maintenance of wakefulness test (MWT) and driving simulation represented the test task to allow us to quantify physiologic changes before, during and after an unwanted event of microsleep. A gradual and sustained decrease in VLF precedes falling-asleep (FA) events by minutes. These changes are regular and recur consistently during MWT and represent most probably a depletion of humoral factors that promote wakefulness. The behavior of the LF/HF represents a low sympatho-vagal balance before FA as a sign of the relaxation taking over. After the FA, there is a surge in this balance signifying an increased stress aimed to overcome the drowsiness. The very significant RRI changes with decreased variability and lower heart rate during FA events confirm the autonomic changes: during a microsleep (MS), there is a decrease in sympathetic drive with increased vagal activity. (ibid G Dorfman Furman et al.)

Thus, there are differences between going to sleep and wakening which are discernable from heart rate variability monitoring providing several minutes of advanced notice before an accident occurs. The first microsleep (MS) during MWT and driving simulator (DS) represented a point for significant changes in all HRV measures. The first accident on DS occurred 2-7 minutes after the first MS. (See: "Investigation of Drowsiness while Driving Utilizing Analysis of Heart Rate Fluctuations", Gabriela Dorfman Furman, Armanda Baharav, Computing in Cardiology 2010; 37:1091-1094.) There are clear HRV markers that indicate sleepiness in sleep deprived subjects. Provided some of these variables show the same trends in sleepy non sleep deprived subjects, a threshold should be defined as to imminent danger of a driver falling asleep at the wheel. (ibid. Gabriela Dorfman Furman et al.)

In another study, the HRV analysis showed that the frequency ratio had a decreasing trend in all subjects as they became drowsy. Although the rate of the decrease was different among individuals, use of a driver drowsiness test can allow the system to learn the properties of a given driver to create personalized drowsiness detection criteria. Pattern recognition analysis using neural networks and in particular combination neural networks as disclosed in U.S. Pat. Nos. 6,445,988 and 6,757,602, among others, is a particularly powerful method of analyzing heartbeats and HRV for the purposes herein, and maybe implemented by the control unit using as input, the heartbeats and/or respiration rate of the vehicle driver or other occupant. Since this technique is discussed at length in the '988 patent, it will not be repeated here.

U.S. Pat. Appln. Publ. No. 20100234747 seems to employ some of the analysis discussed herein but fails to disclose, teach or suggest that the heartbeats can be determined from electric field, optical or other sensors discussed above. Instead, the heartbeats are measured using a steering wheel-mounted sensor causing the problems discussed above with such sensors to arise. Nevertheless, once the heartbeat rate has been obtained, the techniques of this patent application can be applied to predict the onset of sleep up to 10 minutes prior to the event and thus allow sufficient time to warn the driver and to prepare the vehicle system to take control if the driver fails to respond to various tests.

U.S. Pat. Nos. 6,669,632 and 7,397,382 disclose that lung cavity pressure (pleural) can be determined by HRV and is a measure of sleepiness giving another HRV property that can be used to predict the level of drowsiness that the driver is experiencing. Other studies have indicated that even changes in blood pressure can be estimated from HRV.

Thus, there are several ways in which HRV can be used to provide a warning that the driver is about to fall asleep as disclosed in the literature. Most of these methods deal with the heartbeats as normal sine wave cycles. In other studies, the shape of the heartbeat and of the respiration wave contain important information to further refine the falling asleep prediction. Since several methods are disclosed herein as to how to obtain the heartbeat and respiration waves, the particular analysis method will depend on the fidelity of the waves obtained and thus the exact analysis method used will vary depending on the data acquisition method used. One preferred technique that is generally applicable is to use neural networks that have been trained on the system with the chosen data acquisition method.

Detailed discussions of the use and training of neural networks for occupant sensing are disclosed in the patents of the current assignee mentioned herein and incorporated herein by reference and thus will not be repeated here. Generally, the input to the input layer nodes will be the raw heartbeat data with sufficient resolution as to capture the shape of each pulse when this differs from a sine wave, or the periods and amplitudes of the waves when a sine wave is a good approximation to the waves. A neural network can then be trained using a driving simulator using a sufficient number of subjects as to capture the population at large. This can form the basic analysis program which can be modified in use based on measurements of a particular driver. Thus, when the vehicle is driven by a particular person, the system can recognize that this is the case, by face or other biometric recognition, and learn the normal heartbeat and respiration properties of that particular driver. When a new driver takes over, the program can revert to the generic population program.

It is expected that the analysis program will take other information into account when it is available such as the temperature, blood pressure and oxygen level of the blood. This will depend on the particular suite of sensors that are used and such information will not be available, for example, if electric field sensors are the only ones being used. Other information that can also be incorporated includes lane departure, steering wheel motion, vehicle speed and acceleration, time of day, head and body motion, state of the eyes and blinking rates and any other measured properties of the occupant, vehicle and how it is being driven and/or the environment.

Other factors that can be included in the analysis depending on the information available include:

1. Pulse recovery can be aided by removing signals with frequency lower than about 0.67 Hz (40 bmp) and higher than about 1.67 Hz (100 bmp).
2. The heart rate decreases during sleep by about 5-40%.
3. Blood pressure decreases during sleep to about 77-80% of its value when the driver is awake.
4. The total spectrum power and its individual components in absolute values in different sleep stages HF (ms2) 1148±1148 (Wakefulness) 2277±2878 (Stage 2 non-REM) 1777±2789 (Stage 4 non-REM) 2073±3158 (REM sleep)
5. A reduction of the LF/HF ratio in the course of falling asleep.
6. The HRV is much larger during sleep. That is, one beat interval may be about 0.9 seconds and the next one about 1.3 seconds in the sleeping person while in the awake person, about 0.7 to about 0.8 seconds.
7. Typically, the differences in the cardiac dynamics during sleep and wake phases are reflected in the average (higher in sleep) and standard deviation (lower in sleep) of the interbeat intervals.

It is important to keep in mind that EEG results demonstrate that it is feasible to accurately estimate quantitatively driving performance. Thus, the best system will be to measure EEG which is not economically feasible at this time but may be in the future. In particular the Plessey EPIC sensor suite shows promise of providing this capability.

7. Gestures

Use of optical systems to recognize gestures and then control a component has been disclosed in U.S. Pat. Appln. Publ. Nos. 20070057781, 20080048930, 20080143085, 20080065291 and 20080051946. Through the appropriate placement of antennas, electric field systems such as discussed elsewhere herein and marketed by Honda Elesys for occupant sensing can also be configured to respond to gestures by the driver. If the system has concluded that it is time to test the driver for response time as the system has determined that he/she has become drowsy, a warning light, sound or audio request can be delivered and responded to by the driver raising his arm, moving his head, pointing or giving a thumbs up which can be sensed by the electric field system. The audio request can be one of a plurality of different audio requests, each requiring a specific and possibly different responsive action by the driver.

Gesture detection systems have been reported by the MIT Media Lab and referenced elsewhere herein, but these concepts have not been applied to the sensing of gestures in a vehicle. See, for example, "Musical Applications of Electric Field Sensing", Joseph A. Paradiso and Neil Gershenfeld, Draft 1.9, April 1996; to be published in Computer Music Journal and "Talking to the Wall", Kate Greene, MIT Technology Review, May 3, 2011, and U.S. Pat. Nos. 5,844,415 and 5,936,412.

Gestures that are recognized by electric field systems can also be used to control other vehicle components. If a heads up display is present, then the driver can change the display contents by pointing at a selection of the display in a manner that can be recognized by an optical or electric field gesture recognition system. It has been demonstrated that electric field gesture recognition systems can have a high resolution and are capable of measuring displacements on the millimeter scale.

8. Electric Field Wiring Replacement As discussed in various U.S. patents and published applications such as U.S. Pat. Nos. 6,326,704, 7,079,450, 7,889,096, 7,760,080, 7,089,099, 7,880,594, 7,786,864, 7,920,102, 7,467,034, 20080051946, 20080048930, wires and connectors are not only expensive components to make and install in a vehicle, they are also the largest source of warranty repairs. Thus, there is a dire need to eliminate wires and connectors wherever possible. Much of this can be accomplished through use of electric field systems such as the Honda Elesys electric field occupant sensor discussed and referenced elsewhere herein. This invention can be implemented in many ways, only one of which will be discussed here. If a vehicle-wide power door lock switch is present in the driver's door, for example, is replaced by a grounded metal plate having approximately the same area and the plate is connected to ground, then when the driver, of a vehicle with an electric field antenna in the driver seat touches the plate, the electric field is shorted to ground and the current in the seat antenna will change in a detectable manner. Thus, a door operated switch can be replaced by a metal plate. The electric field system would quickly get confused if there were more than one such switch having a different function.

This problem can be solved by connecting the switch to ground through an impedance. This can be in the form of a resistance, but this might require that every driver have the same conductance and thus another solution is preferred. If the electrical field creating circuit can vary its frequency and if the plate switch is connected to ground through a resonating circuit, then the electric field system would show a maximum or minimum current as a function of frequency and if each switch was tuned to a different frequency, then they could each respond differently resonating, for example, at a different frequency. One skilled in the art can now find or develop many other circuit designs that would allow one switch to be distinguishable from another so this invention is not limited to the tuned circuit design. By this manner, much of the wiring, many of the switches and many of the connectors can be eliminated from the vehicle, reducing its cost and reducing its maintenance costs.

The switch need not be a metal plate and can be anything that is conductive and connected to ground through an impedance or other electrical circuit or element. In some cases, it might be desirable to retain the switch but instead of connecting it to the vehicle electrical system, it is connected to ground as in the plate example above. In this case, the vehicle occupant would connect the impedance to ground by depressing the switch. This can be desirable when the duration of switch closure is used to control the degree of window opening, for example.

9. Discussion of Electromagnetic Occupant Sensors

What follows now is a general discussion of electromagnetic occupant sensors which also appears in other of the assignee's patents and patent applications. Electric field sensors and wave sensors are sometimes similar from the point of view of sensing the presence of an occupant in a vehicle. In both cases, a time varying electric field, a form of a time-varying signal, is generated and directed into the volume of the passenger compartment and then disturbed or modified by the presence of the occupant. Different occupants or occupying items will cause different disturbances or modifications. At high frequencies in the visual, infrared and high frequency radio wave region, the sensor is based on its capability to sense a change of wave characteristics of the electromagnetic field, such as amplitude, phase or frequency. As the frequency drops, other characteristics of the field are measured. At still lower frequencies, the occupant's dielectric properties modify parameters of the reactive electric field in the occupied space between or near the plates of a capacitor. In this latter case, the sensor senses the change in charge distribution on the capacitor plates by measuring, for example, the current wave magnitude or phase in the electric circuit that drives the capacitor. These measured parameters are directly connected with parameters of the displacement current in the occupied space. In all cases, the presence of the occupant reflects, absorbs or modifies the waves or variations in the electric field in the space occupied by the occupant.

When different objects are placed on the front driver or passenger seat, the images from imagers, for example, are different but there are also similarities between all images of rear facing child seats, for example, regardless of where on the vehicle seat it is placed and regardless of what company manufactured the child seat. Alternately, there will be similarities between all images of people sitting on the seat regardless of what they are wearing, their age or size. The problem is to find the "rules" which differentiate the images of one type of object from the images of other types of objects, e.g., which differentiate the occupant images from the rear facing child seat images. The similarities of these images for various child seats are frequently not obvious to a person looking at plots of the time series and thus computer algorithms are developed to sort out the various patterns. For a more detailed discussion of pattern recognition, see, for example, U.S. Pat. No. RE 37,260.

Determination of these rules is important to the pattern recognition techniques used in at least one of the inventions disclosed herein such as the optical monitoring of the face of the driver. In general, three approaches have been useful, artificial intelligence, fuzzy logic and artificial neural networks (including cellular and modular or combination neural networks and support vector machines—although additional types of pattern recognition techniques may also be used, such as sensor fusion). In some implementations, the rules are sufficiently obvious that a trained researcher can sometimes look at the returned signals and devise a simple algorithm to make the required determinations. In others, such as the determination of the presence of a rear facing child seat or of an occupant, artificial neural networks can be used to determine the rules.

Electromagnetic energy based occupant sensors exist that use many portions of the electromagnetic spectrum. A system based on the ultraviolet, visible or infrared portions of the spectrum generally operate with a transmitter and a receiver of reflected radiation. The receiver may be a camera or a photo detector such as a pin or avalanche diode. At other frequencies, the absorption of the electromagnetic energy is primarily used and at still other frequencies, the capacitance or electric field influencing effects are used. Generally, the human body will reflect, scatter, absorb or transmit electromagnetic energy in various degrees depending on the frequency of the electromagnetic waves.

In an embodiment wherein electromagnetic energy is used, any portion of the electromagnetic signals that impinges upon, surrounds or involves a body portion of the occupant is at least partially absorbed by the body portion. Sometimes, this is due to the fact that the human body is composed primarily of water, and that electromagnetic energy of certain frequencies is readily absorbed by water. The amount of electromagnetic signal absorption is related to the frequency of the signal, and size or bulk of the body portion that the signal impinges upon. For example, a torso of a human body tends to absorb a greater percentage of electromagnetic energy than a hand of a human body.

Thus, when electromagnetic waves or energy signals are transmitted by a transmitter, the returning waves received by a receiver provide an indication of the absorption of the electromagnetic energy. That is, absorption of electromagnetic energy will vary depending on the presence or absence of a human occupant, the occupant's size, bulk, surface reflectivity, etc. depending on the frequency, so that different signals will be received relating to the degree or extent of absorption by the occupying item on the seat. The receiver will produce a signal representative of or corresponding to the returned waves or energy signals which will thus constitute an absorption signal as it corresponds to the absorption of electromagnetic energy by the occupying item in the seat.

One or more of the transducers can also be image-receiving devices, such as cameras, which take images of the interior of the passenger compartment including the face of the driver. These images can be transmitted to a remote facility to monitor the passenger compartment or can be stored in a memory device for use in the event of an accident, i.e., to determine the status of the occupant(s) of the vehicle prior to the accident. In this manner, it can be ascertained whether the driver was falling asleep, talking on the phone, etc. Alternately, the images can be forwarded to a remote monitoring site when the driver fails to respond to the determination of the systems described herein that he/she is falling asleep, having a heart attack, under the influence of drugs or otherwise unable to effectively operate the vehicle. The remote site can observe and monitor the driver and issue verbal instructions as to what action the driver should take. If the driver fails to heed the directions then the vehicle can be gradually immobilized using technology available today.

A memory device for storing images of the passenger compartment, and also for receiving and storing any other information, parameters and variables relating to the vehicle or occupancy of the vehicle, may be in the form of a standardized "black box" (instead of or in addition to a memory part in a processor). The IEEE Standards Association is currently beginning to develop an international standard for motor vehicle event data recorders. The information stored in the black box and/or memory unit in the processor, can include the images of the interior of the passenger compartment including the face of the driver as well as the number of occupants and the health state of the occupant(s). The black box would preferably be tamper-proof and crash-proof and enable retrieval of the information after a crash.

In addition to the heartbeat and respiration sensors discussed so far, it should be noted that radar-based sensors can also be used such as disclosed in patents referenced herein. Radar also can be used to determine the presence and location of occupants in a vehicle. For example, a heartbeat sensor based on micropower impulse radar (MIR) is disclosed in McEwan, U.S. Pat. Nos. 5,573,012, 5,361,070 and 5,766,208. This heartbeat sensor can be positioned at any convenient position relative to the seats where occupancy is being monitored. A preferred location is within the vehicle seatback. This MIR sensor as disclosed in these patents is to determine the presence of a heartbeat and not used to disclosed the health and fatigue state of the driver as disclosed herein.

Various means by which the driver can provide feedback have been discussed above. Another method which can be applicable when a camera is used is to allow for a gesture response. Perhaps the driver has a speaking impediment and the system requires a spoken response to the interrogation. In such cases, an alternative can be provided whereby the driver indicates his response through a hand and/or head motion. As long as it is the expected motion, this response can be acceptable. A sophisticated algorithm can interpret a gesture, for example, that may be in response to a question from the computer system (conveyed on a display or vocalized using a speaker). The question may be one of a plurality of different questions, so that the same gesture can be used in response to multiple questions and interpreted only in consideration of the posed question. The driver may indicate by a gesture, within a reasonable time after the posing of the question, that he or she is OK and the system can then interpret a "thumbs up" gesture for such an OK response. A very large number of options exist that can be entirely executed by the combination of voice, speakers and a camera that can see gestures. When the system does not understand, it can ask to have the gesture repeated, for example, or it can ask for a confirmation.

A living object such as an animal or human has a fairly high electrical permittivity (Dielectric Constant) and relatively lossy dielectric properties (Loss Tangent) absorbs a lot of energy when placed in an appropriate varying electric field. This effect varies with the frequency. If a human, which is a lossy dielectric, is present in the detection field, then the dielectric absorption causes the value of the capacitance of the object to change with frequency. For a human (poor dielectric) with high dielectric losses (loss tangent), the decay with frequency will be more pronounced than for objects that do not present this high loss tangency. Exploiting this phenomena it is possible to detect the presence of an adult, child, baby or pet that is in the field of the detection circuit.

Since people differ in their operation of a vehicle and response times, there will likely be some training of the processor required, e.g., training of the pattern recognition technique therein or determining the acceptable normal response time for a given driver. That is, the processor may be programmed to vary the acceptable response time indicative of alertness of a driver for different drivers, so that one response time for one driver may be acceptable while the same response time for another driver may be indicative of that driver being incapacitated. Moreover, the direction of the road ahead can be determined soon after driving begins as the driver will most likely be looking at the road at least at the start of his trip and for most of his driving time. Tracking the head from that point forward, based even on a camera overhead, is expected to be relatively easy and the direction of gaze determined. Although it would be beneficial to also monitor the driver's eyes or eye lids, it may not justify the cost of a special, additional system just for that purpose. The driver can fall asleep with his gaze unchanged so in addition to motion of the driver's head, motion of the steering wheel, the position of the vehicle relative to the lane (as determined from an outside looking camera) may be monitored and analyzed in combination therewith to enable a determination of the driver's ability to operate the vehicle. With respect to monitoring of the steering wheel, which may be effected by a sensor that monitors rotation of the steering wheel relative to the steering column, lack of turning of the steering wheel or erratic, uncontrolled turning of steering wheel would be an excellent confirmatory indication of the driver falling asleep.

Other training of the processor or pattern recognition technique used thereby can involve motion statistics that lead to an expectation as to what a particular driver does when he is alert. If the driver passes the test, then the thresholds can be modified. In particular, as a person begins to fall asleep, he can execute some jerking motions or other telltale motions that will be different from his normal alert behavior. Any such out-of-the-ordinary movements can evoke the test of his response time. Such unordinary movements can be programmed into the trained pattern recognition technique in the processor, i.e., embodied on computer-readable medium accessible by the processor, so that once one of these movements is detected by the pattern recognition technique in the processor, the processor would control the reactive component(s) accordingly, or otherwise monitor detection of a response to cue or other required response by the driver indicating alertness.

Although optical monitoring of the driver's head or part thereof is most likely to enable an adequate determination of whether the driver is falling asleep or otherwise unable to operate the vehicle, other types of systems for monitoring the driver may be used alone or in combination with the optical monitoring system, including ultrasonic sensors, electric field sensors, bladder sensors, heartbeat sensors, respiration sensors and/or strain gage weight sensors to aid in this determination. In this case, the processor would be coupled to, for example, the strain gage weight sensors which provide an indication of the weight distribution of the occupant, and would analyze both the images obtained by the optical imaging system and the data provided by the strain gage weight sensors in order to make the determination of the driver's ability to operate the vehicle. Also, a liquid-filled bladder could be placed in contact with the driver on the seat and the heart rate and breathing can be monitored thereby (see, e.g., U.S. Pat. No. 3,727,606), and/or an EKG can be picked up with conductors put into the seat surface (see, e.g., U.S. Pat. No. 3,954,100) or by a Pessey ECG sensor such as PS2501. These would provide additional data for use by the processor when making the determination as to whether the driver is falling asleep or otherwise unable to operate the vehicle. Any such sensors may be coupled by wiring or wirelessly to the processor.

Additional data for use by the processor may include data from an accelerometer arranged in seatbelt and coupled to the processor. Such an accelerometer is designed to measure the heartbeat and/or respiration of the driver which could be correlated to and used in a determination by the processor that the driver is falling asleep or otherwise unable to operate the vehicle. Further, the precise motion of the chest of the occupant may be determined using a laser, for example, arranged in front of the driver, e.g., in the dashboard. The laser would also be coupled to the processor which would use the data from the laser in its determination of the attentiveness or alertness of the driver. This could be a low cost way of monitoring respiration of the driver, which is correlated to the driver's ability to operate the vehicle. If the laser operates in the terahertz frequency range, it can pass through the driver's clothes and reflect off of the driver's chest providing a more accurate motion of the chest.

As for additional or alternative reactive components to the audible and visual devices described above, the processor which makes the determination of the driver's ability to operate the vehicle may also be arranged to control a system which generates a cue such as an audio request for the driver to "look at the road", generates a rumble strip sound over the speakers in the vehicle and/or generates a vibration of the seat and/or steering wheel. When people run over a rumble strip, the natural reaction would be to look at the road. In that case, the driver would not have to be trained to, for example, depress the horn button. If he or she shifted his or her gaze in response to the rumble strip noise, that would be a sufficient response and the reaction time can be measured. Thus, the continued monitoring of the driver's head by the processor after the determination of the driver's inability to operate the vehicle is used to determine the driver having regained the ability to operate the vehicle.

Other reactive components may be coupled to the processor and perform cognitive tests including requiring an oral response, visual response or gesture response, for example, to the cue. Thus, the reactive component may be one which requires feedback from the driver, i.e., a detection of speech. In other words, if the driver is already looking at the road, then he can orally tell the system that he is awake and attentive.

Some of the applications above have been based on the idea of training a neural network or modular neural network (MNN) and then installing it in the vehicle where it does not change. When determining whether a driver is asleep or otherwise incapacitated and unable to operate a vehicle, it would be beneficial to be able to compare an individual's behavior over time but it is difficult to make a special training session for each individual. Such a training session for each driver of the vehicle is within the scope of the invention and may be useful when a particular driver is the sole or one of the few drivers of a vehicle, such as for municipal transportation systems. In other situations, some of the parameters of the neural network can be made adaptive, that is they change over time as the system adapts to a particular individual.

The trained pattern recognition technique applied by the processor may be trained on all measures of occupant behavior that might indicate driver attentiveness or lack thereof while driving, i.e., whether the vehicle is moving or not. For example, vehicle parameters may also be analyzed such as acceleration, steering wheel angle, angular motion of the vehicle, etc. This would be especially useful if accurate maps were available so that it is known where the vehicle is relative to the lane boundaries. The attempted running of stop lights and stop signs would be a clear indication of lack of attentiveness that can be used if maps or an external viewing camera were present, and indicate the presence of stop lights and stop signs, or other objects, to which the driver has not respected. Probe vehicles may be used to map roads for attentiveness purposes, so that once a map is obtained and installed on the vehicle, the processor may access the map and determine whether a change in the driver's head position and/or use of the steering wheel is the result of the driver falling asleep or simply following a curvature in the road. If a map is not available, then the processor could be designed to include the motions of drivers on the same stretch of road and then measure the driving behavior of the driver compared with the other vehicle drivers on the same stretch of road to determine inattentiveness. The expected behavior of a driver on a stretch of road may even be included in the map. Map updating techniques may be used to ensure that the processor on the vehicle that is analyzing the driver's action relative to data from the map is up-to-date.

Another factor to be used by the processor is the amount of time when driver is not looking at the road ahead. If this exceeds, e.g., 2 seconds, then the processor could use this factor in its determination of inattentiveness. Yet another factor is head orientation which may be determined by analysis of the images of the driver. Most of the time the driver is looking forward, so the position in which the driver's head is in most of the time may be considered the normal position and variations from this position for an extended period of time may be indicative of the driver's inattentiveness.

Numerous studies have shown that changes in steering activity are correlated with driver state of impairment. Monitoring vehicle output as reflected by control of the steering wheel, rather than driver actions, is a less obtrusive test and may be combined with the optical monitoring systems described above. Without a map, the system can be fooled by heavy traffic or a winding road. Nevertheless, if the reactive component is a simulated rumble strip sound and the driver quickly reacts, then it is known that the driver is alert and the road is at fault. The threshold for steering, for example, can then be temporarily changed.

An even more sophisticated system of monitoring the behavior of the driver is to track his eye motions using such techniques as are described in U.S. Pat. Nos. 4,648,052, 4,720,189, 4,836,670, 4,950,069, 5,008,946 and 5,305,012. Detection of the impaired driver in particular can be best determined by these techniques. These systems use pattern recognition techniques plus, in many cases, the transmitter and CCD receivers must be appropriately located so that the reflection off of the cornea of the driver's eyes can be detected as discussed in the patents mentioned herein. The size of the CCD arrays used herein permits their location, sometimes in conjunction with a reflective windshield, where this corneal reflection can be detected with some difficulty. Sunglasses or other items can interfere with this process.

SUMMARY

The foregoing structure enables significant advantages to be obtained. For example, the foregoing structure and methods for using the structure provide new and improved methods and systems for monitoring a driver of a vehicle to determine whether the driver is falling asleep or otherwise unable to operate the vehicle, new uses of electric field sensors to determine the heartbeat and/or respiration rates of the driver and/or other occupants of a vehicle, to interrupt vehicle occupant gestures for the control of one or more vehicle components and/or to replace vehicle mechanical or electrical switches, connectors and/or wires, new monitors that monitor the health state of one or more vehicle occupants based on measurements of their heartbeat and respiration rates, and new uses of optical sensors to determine the heartbeat and/or respiration rates of the driver and/or other occupants of a vehicle.

Furthermore, the invention provides for new uses of weight sensors, such as bladders, strain gages, load sensors and/or displacement sensors, to determine the heartbeat and/or respiration rates of the driver and/or other occupants of a vehicle, new uses of radar-based sensors or accelerometers to determine the heartbeat and/or respiration rates of the driver and/or other occupants of a vehicle, and new analyzers that analyze the heartbeat and/or respiration rates of the driver and/or other occupants of a vehicle to determine the state of drowsiness or health state of the driver or other occupant of a vehicle. The invention also contemplates use of any of these apparatus and methods to control a vehicle component.

Among the inventions disclosed above is a vehicle including a system for monitoring a driver of the vehicle in accordance with the invention includes a frame, an electric field occupant sensing and monitoring system arranged to monitor periodic changes in an electric field caused by a driver's heartbeat and/or respiration as well as possibly motion of the driver and parts of the driver. Signal processing algorithms are provided to separate the signals from the heartbeat, respiration and occupant motion to be analyzed separately.

The vehicle can have, in addition to or as a substitution for, the electric field monitoring system, an optical imaging system arranged on the frame to obtain images of the driver, and a processor coupled to the optical imaging system and arranged to analyze the images obtained by the optical imaging system to locate a head of the driver in the images and monitor the driver's head or a part thereof over time, e.g., for movement of the driver's head or part thereof. The imaging system is particularly arranged to monitor the face of the driver to obtain information related to the heart rate, respiration rate, temperature and/or blood pressure of the driver. The processor also determines, based on the monitoring of the driver's head or face or a part thereof, whether the driver has lost the ability to operate the vehicle.

The loss of ability to operate the vehicle can arise from the driver falling asleep or otherwise being incapacitated due to the effects of alcohol or drugs or of a medical condition such as a heart attack, stroke or seizure. A reactive component on the vehicle is affected by the determination by the processor that the driver has lost or is in danger of losing the ability to operate the vehicle, and can require a responsive action by the driver to indicate regaining the ability to operate the vehicle or, in lieu of an appropriate responsive action, can exert control over the vehicle to slow the vehicle and bring it to a stop. The processor may use a trained pattern recognition technique when monitoring the driver's head, face or part thereof, e.g., when locating the head or face of the driver or part of the driver's head or face in the obtained images.

The optical imaging system may include a plurality of optical imagers spaced apart from one another and each positioned to obtain images of a face of the driver. The processor monitors the driver's head in one embodiment by determining a position of the head of the driver in images obtained at different times and analyzing the determined position of the head of the driver in the different images. In another embodiment, the processor monitors the driver's eyes by determining a position of the eyes of the driver in images obtained at different times and analyzing the determined position of the eyes of the driver in the different images. In yet another embodiment, the processor monitors the driver's eye lids by determining a position of the eye lids of the driver in images obtained at different times and analyzing the determined position of the driver's eye lids in the different images. In still another embodiment, the processor monitors the face of the driver or a part thereof and determines one or more of the heartbeat, respiration rate, blood pressure, and temperature.

The reactive component, of which there may be one or more, may be a warning light, an alarm light, a warning sound generator, a tactile sensation generator, and a voice generating device. More generally, the reactive component may be warning system or alarm system, which provides one or more audible, tactile, visual warnings. Each reactive component could be controlled differently depending on the monitoring of the driver's head, face or part thereof or of the heartbeat, respiration rate, blood pressure, temperature or motion. One reactive component may be a button which, when pressed, indicates that the driver has regained the ability to operate the vehicle. Another may be a microphone and associated voice recognition software. The processor may also operate the horn and lights of the vehicle, or other externally apparent warning or alarm system, after determining that the driver is falling asleep or otherwise incapacitated to warn other vehicles of the inability of the driver to operate the vehicle. The driver may also be required to react by providing an audio signal such as by enunciating one or more spoken words.

Also disclosed above is a method for monitoring operation of a vehicle by a driver that includes obtaining images of the driver from at least one vehicle-mounted optical imager, analyzing the obtained images to locate a head of the driver in the images, monitoring the driver's head or a part thereof over time, determining, based on the monitoring of the driver's head or part thereof, whether the driver has lost the ability to operate the vehicle, the lost of ability to operate the vehicle arising from the driver falling asleep or otherwise being incapacitated, and upon a determination that the driver has lost the ability to operate the vehicle, affecting a reactive component which requires action by the driver to indicate regaining of the ability to operate the vehicle or exerts control over the vehicle to slow the vehicle and bring it to a stop.

Monitoring the driver's head or a part thereof over time may entail training a pattern recognition technique to locate the head of the driver or other part of the driver. Monitoring the driver's head or a part thereof over time may entail determining a position of the head of the driver in images obtained at different times and analyzing the determined position of the head of the driver in the different images. When monitoring the driver's head or a part thereof over time comprises monitoring the driver's eyes, this monitoring may include determining a position of the eyes of the driver in images obtained at different times and analyzing the determined position of the eyes of the driver in the different images. When monitoring the driver's head or a part thereof over time entails monitoring the driver's eye lids, this monitoring may include determining a position of the eye lids of the driver in images obtained at different times and analyzing the determined position of the driver's eye lids in the different images. When monitoring the driver's head over time or a part thereof entails monitoring a portion of the skin of the driver's face, this monitoring may include selecting an appropriate skin portion, illuminating that portion, perhaps with non-visible electromagnetic radiation, and tracking that portion in subsequent images in order to determine the variation in one or more properties of the skin portion in order to determine at least one of the temperature, heartbeat, respiration rate and blood pressure as expressed in the skin patch or the capillaries thereof.

In one embodiment of the invention, one or more biological properties of the driver is/are obtained by filtering the signals from one or more electric field sensors and monitoring one or more frequency ranges indicative of one or more of the heartbeat rate, respiration rate and bodily motion of the driver in order to determine that the driver may be: falling asleep; experiencing a heart attack, stroke or seizure; or is under the influence of alcohol and/or drugs.

Other systems and methods which are capable of monitoring the heart rate, respiration rate, blood temperature or other vital signs of the driver include fluid-filled bladders, pressure mats, Plessey ECG sensors, radar-based and other occupant sensors such as disclosed in the patents and patent application publications mentioned herein.

If, by any of these systems or methods, it is determined that the driver may not be able to effectively operate the vehicle, the driver can be alerted and the system may then require a timely response from the driver before any action is taken by a vehicle component.

Electric Field (EF) Applications

A primary method disclosed above involves expanding in what is considered to be an unobvious manner, use of electric field (EF) sensors such as being marketed by Honda Elesys for detection and classification of passenger occupants in a vehicle for the purpose of airbag suppression. In addition to the measurement of heart and respiration rates and their variability and anomalies, other non-obvious uses have been disclosed, such as for communication to a vehicle system using gestures and the elimination of wires associated with vehicle switches. These make use of several properties of electric fields including operation in the loading, transmitting and shunting modes. (Musical Applications of Electric Field Sensing, April, 1996).

Combinations of Methods

Methods described herein for using the heartbeat and respiration rates for determining drowsiness can be combined with each other as well as with other methods, disclosed herein or elsewhere, or otherwise known or applied in the field to which this invention pertains, such as optical eye closure monitoring methods, in order to improve the forecasting accuracy and reduce false alarms. These other measures can include a physiological diagnostic based on the eyelid motion observation and a behavioral diagnostic based on the observation of the vehicle lateral control behavior. They can be combined with additional in-vehicle and contextual information to provide a final decision about the driver's vigilance state, as reported in the literature.

Although the primary application of technology disclosed above is for preventing accidents caused by driver drowsiness, other applications are to apply the technology to airplane pilot and train conductors (or more generally vehicular operators) and other passengers in automobiles and planes (or more generally vehicular occupants) to detect medical conditions that should receive immediate attention, such as heart attacks, seizures and strokes as will be discussed below.

Although several preferred embodiments are illustrated and described above, there are possible combinations using other geometries, sensors, materials and different dimensions for the components that perform the same functions. At least one of the inventions disclosed herein is not limited to the above embodiments and should be determined by the following claims. There are also numerous additional applications in addition to those described above. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention which is limited only by the following claims.

Preferred embodiments of the invention are described below and unless specifically noted, it is the applicant's intention that the words and phrases in the specification and claims be given the ordinary and accustomed meaning to those of ordinary skill in the applicable art(s). If the applicant intends any other meaning, they will specifically state they are applying a special meaning to a word or phrase.

Likewise, applicant's use of the word "function" here is not intended to indicate that the applicant seeks to invoke the special provisions of 35 U.S.C. §112, sixth paragraph, to define his invention. To the contrary, if applicant wishes to invoke the provisions of 35 U.S.C. §112, sixth paragraph, to define his invention, he will specifically set forth in the claims the phrases "means for" or "step for" and a function, without also reciting in that phrase any structure, material or act in support of the function. Moreover, even if applicant invokes the provisions of 35 U.S.C. §112, sixth paragraph, to define his invention, it is the applicant's intention that his inventions not be limited to the specific structure, material or acts that are described in the preferred embodiments herein. Rather, if applicant claims his inventions by specifically invoking the provisions of 35 U.S.C. §112, sixth paragraph, it is nonetheless his intention to cover and include any and all structure, materials or acts that perform the claimed function, along with any and all known or later developed equivalent structures, materials or acts for performing the claimed function.

In the context of this document, computer-readable medium could be any means that can contain, store, communicate, propagate or transmit a program for use by or in connection with the method, system, apparatus or device. The computer-readable medium can be, but is not limited to (not an exhaustive list), electronic, magnetic, optical, electromagnetic, infrared, or semi-conductor propagation medium. The medium can also be (not an exhaustive list) an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM). The medium can also be paper or other suitable medium upon which a program is printed, as the program can be electronically captured, via for example, optical scanning of the paper or other medium, then compiled, interpreted, or otherwise processed in a suitable manner, if necessary, and then stored in a computer memory. Also, a computer program or data may be transferred to another computer-readable medium by any suitable process such as by scanning the computer-readable medium.

The invention claimed is:

1. A vehicle, comprising:
a seat in which an occupant sits during use of the vehicle; and
a monitoring system for monitoring the occupant in said seat, said monitoring system comprising:
a plurality of sets of electric field antennas, each of said sets including at least one antenna;
a control unit connected to said sets of antennas, said control unit including selectors coupled to said antennas and controlling said selectors to obtain signals from one or more of said antennas serving as receiving antennas and one or more of said antennas serving as sending antennas, said control unit determining which combination of one or more of said antennas serving as the sending antennas and one or more of said antennas serving as the receiving antennas provides a strongest signal in at least one of an expected heartbeat range and an expected respiration range of the occupant and then monitoring this determined combination for at least one of changes and deviations from a normal range of at least one of heartbeats and respiration rate.

2. The vehicle of claim 1, wherein said control unit periodically re-obtains signals from different combinations of one or more of said antennas serving as the sending antennas and one or more of said antennas serving as the receiving antennas to determine, each time, which combination of one or more of said antennas serving as the sending antennas and one or more of said antennas serving as the receiving antennas provides a strongest signal.

3. The vehicle of claim 1, wherein said sets of electric field antennas are arranged in said seat, embedded in said seat or arranged as part of cover material of said seat.

4. The vehicle of claim 1, wherein said seat is a driver's seat.

5. The vehicle of claim 4, further comprising:
a steering wheel arranged in front of said seat; and
an additional antenna arranged on said steering wheel and connected to said control unit.

6. The vehicle of claim 1, wherein each of said sets of electric field antennas comprises at least two antennas.

7. The vehicle of claim 1, further comprising:
a ceiling or headliner arranged above said seat; and
an additional antenna arranged on said ceiling or headliner above said seat and connected to said control unit.

8. The vehicle of claim 1, further comprising:
a side door arranged alongside said seat; and
an additional antenna arranged on said side door and connected to said control unit.

9. The vehicle of claim 1, further comprising:
a floor arranged below said seat; and
an additional antenna arranged on said floor and connected to said control unit.

10. The vehicle of claim 1, further comprising:
a seatbelt associated with said seat; and
an additional antenna arranged on or in said seatbelt and connected to said control unit.

11. The vehicle of claim 1, wherein said seat has a back portion and a bottom portion, at least one of said sets of antennas being arranged in said back portion and at least one of said sets of antennas being arranged in said bottom portion.

12. The vehicle of claim 1, wherein said seat is a passenger's seat, further comprising at least one sensor selected from a group consisting of a weight sensor, an optical sensor, an ultrasonic sensor, a seat track sensor and a seatback sensor, said at least one sensor being associated with said seat and coupled to said control unit, said control unit processing data provided by said at least one sensor when monitoring the at least one of the heartbeat and respiration range of the occupant for at least one of changes and deviations from a normal range of at least one of heartbeats and respiration rate.

13. The vehicle of claim 1, wherein said seat is a driver's seat, further comprising a notification system that notifies the occupant of said seat of their inability to operate the vehicle and requires responsive action by the occupant when said control unit determines at least one of changes and deviations from the normal range of at least one of heartbeats and respiration rate.

14. The vehicle of claim 13, wherein said control unit is configured to analyze the responsive action by the occupant, if any, to the notification and control vehicle operation when the responsive action is indicative of the occupant being unable to operate the vehicle safely.

15. The vehicle of claim 1, wherein said control unit is configured to obtain normal heartbeat and respiration rates for the occupant from one or more combinations of sending and receiving antennas and compare at least one of a current heartbeat and respiration rate for the same occupant to at least one of the normal heartbeat and respiration rates to determine at least one of changes and deviations therefrom.

16. The vehicle of claim 1, wherein said seat is a driver's seat and said control unit is configured to monitor the determined combination of said antennas by analyzing oscillation of intervals between consecutive heartbeats to determine whether the occupant of said seat is becoming drowsy or falling asleep.

17. The vehicle of claim 1, wherein said seat is a driver's seat and said control unit is configured to monitor the determined combination of said antennas for at least one of changes and deviations from a normal range of at least one of heartbeats and respiration rate using pattern recognition techniques.

18. A method for monitoring an occupant of a vehicle, comprising:
   arranging a plurality of antennas on a seat, each separated from one another;
   selecting from a plurality of different possible combinations of the antennas, two or more of the antennas to form a sending and receiving arrangement of antennas;
   generating a weak electric field via the selected antenna arrangement;
   detecting information related to a current flow in the selected antenna arrangement during generation of the weak electric field; and
   determining, using a processor, a health condition of the occupant based on the detected information.

19. The method of claim 18, further comprising obtaining normal data about the health condition of the occupant based on the detected information at one instance, the step of determining, using the processor, the health condition of the occupant based on the detected information comprising comparing information detected at another, later instance to the normal data.

20. The method of claim 18, further comprising:
   notifying the occupant of a change in their health condition relating to their inability to safely operate the vehicle;
   requiring the occupant to generate a response to the notification;
   monitoring the occupant for the response to the notification; and then
   controlling vehicular operation based on the monitoring of the occupant for the response to the notification.

21. A vehicle, comprising:
   a seat in which a driver or operation of the vehicle sits during use of the vehicle; and
   a monitoring system for monitoring the driver in said seat, said monitoring system comprising:
      a plurality of sets of electric field antennas, each of said sets including at least one antenna;
      a control unit connected to said sets of antennas, said control unit including selectors coupled to said antennas and controlling said selectors to obtain signals from one or more of said antennas serving as receiving antennas and one or more of said antennas serving as sending antennas, said control unit determining which combination of one or more of said antennas serving as the sending antennas and one or more of said antennas serving as the receiving antennas provides a strongest signal in at least one of an expected heartbeat range and an expected respiration range of the driver and then monitoring this determined combination for at least one of changes and deviations from a normal range of at least one of heartbeats and respiration rate; and
   a notification system coupled to said monitoring system and that notifies the driver of their potential inability to operate the vehicle based on analysis of at least one of changes and deviations from a normal range of at least one of heartbeats and respiration rate and that is configured to require responsive action by the driver when said control unit determines at least one of changes and deviations from the normal range of at least one of heartbeats and respiration rate.

22. The vehicle of claim 21, wherein said control unit is configured to analyze the responsive action by the driver, if any, to the notification provided by said notification system and control vehicle operation when the responsive action is indicative of the driver being unable to operate the vehicle safely.

23. The vehicle of claim 21, wherein said control unit is configured to obtain at least one of normal heartbeat and respiration rates for the driver from one or more combinations of sending and receiving antennas, the at least one of normal heartbeat and respiration rates being stored in a memory component accessible by said control unit, and compare at least one of a current heartbeat and respiration rate for the same driver to the at least one normal heartbeat and respiration rates to determine at least one of changes and deviations therefrom.

24. The vehicle of claim 21, wherein said control unit is configured to monitor the determined combination of said antennas by analyzing oscillation of intervals between consecutive heartbeats to determine whether the driver is becoming drowsy or falling asleep.

25. The vehicle of claim 21, wherein said control unit is configured to monitor the determined combination of said antennas for at least one of changes and deviations from a normal range of at least one of heartbeats and respiration using pattern recognition techniques.

* * * * *